(12) United States Patent
Bollu et al.

(10) Patent No.: US 8,338,431 B2
(45) Date of Patent: Dec. 25, 2012

(54) PHOSPHODIESTERASE INHIBITORS

(75) Inventors: Ravindra Babu Bollu, Andhra Pradesh (IN); Jakob Felding, Charlottenlund (DK); Simon Feldbæk Nielsen, Herlev (DK); Jens Christian Højland Larsen, Lyngby (DK)

(73) Assignee: Leo Pharma A/S, Ballerup (DK)

( * ) Notice: Subject to any disclaimer, the term of this patent is extended or adjusted under 35 U.S.C. 154(b) by 493 days.

(21) Appl. No.: 12/528,649

(22) PCT Filed: Feb. 26, 2008

(86) PCT No.: PCT/DK2008/000080
§ 371 (c)(1),
(2), (4) Date: Dec. 14, 2009

(87) PCT Pub. No.: WO2008/104175
PCT Pub. Date: Sep. 4, 2008

(65) Prior Publication Data
US 2010/0099688 A1    Apr. 22, 2010

Related U.S. Application Data

(60) Provisional application No. 60/903,849, filed on Feb. 28, 2007, provisional application No. 60/946,849, filed on Jun. 28, 2007.

(51) Int. Cl.
| | |
|---|---|
| A61K 31/497 | (2006.01) |
| A61K 31/4433 | (2006.01) |
| A61K 31/382 | (2006.01) |
| A61P 17/00 | (2006.01) |
| A61P 35/00 | (2006.01) |
| A61P 29/00 | (2006.01) |
| C07D 213/02 | (2006.01) |
| C07D 491/10 | (2006.01) |
| C07D 241/10 | (2006.01) |
| C07D 335/04 | (2006.01) |

(52) U.S. Cl. .......... 514/255.05; 514/278; 514/432; 544/230; 546/19; 549/23

(58) Field of Classification Search .......... 514/255.05, 514/278, 432; 544/230; 546/15; 549/23
See application file for complete search history.

(56) References Cited

U.S. PATENT DOCUMENTS
2002/0128290 A1    9/2002 Ohshima et al.

FOREIGN PATENT DOCUMENTS
| EP | 0 943 613 A1 | 9/1999 |
|---|---|---|
| EP | 1 029 860 A1 | 8/2000 |
| WO | WO-97/44337 A1 | 11/1997 |

OTHER PUBLICATIONS

Vippagunta et al., Advanced Drug Delivery Reviews, vol. 48, p. 3-26 (on p. 3), 2001.*
CAS RN compound 109264-30-4 (1987).*

* cited by examiner

*Primary Examiner* — Yong Chu
(74) *Attorney, Agent, or Firm* — Birch, Stewart, Kolasch & Birch, LLP

(57) ABSTRACT

The present invention relates to a compound according to formula I,

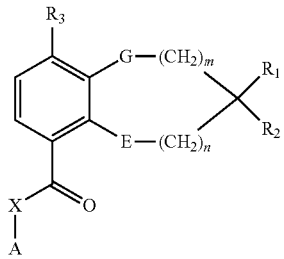

wherein X, A, G, E, $R_1$, $R_2$, $R_3$ are as shown herein; and pharmaceutically acceptable salts, hydrates, N-oxides or solvates hereof. The invention further relates to said compounds for use in therapy, to pharmaceutical compositions comprising said compounds, to methods of treating diseases, e.g. dermal diseases, with said compounds, and to the use of said compounds in the manufacture of medicaments.

25 Claims, No Drawings

PHOSPHODIESTERASE INHIBITORS

This application is the National Phase of PCT/DK2008/000080 filed on Feb. 26, 2008, which claims priority under 35 U.S.C. 119(e) to U.S. Provisional Application Nos. 60/903,849 filed on Feb. 28, 2007, and 60/946,849 filed on Jun. 28, 2007, all of which are hereby expressly incorporated by reference into the present application.

FIELD OF THE INVENTION

The present invention relates to novel compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma, inflammatory bowel disease and COPD. The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra).

Recently developed PDE-4 inhibitors are for example disclosed in EP 0771794 and EP 0943613. WO 96/31476 discloses structurally different 4-substituted-3,5-dichloropyridines which are inhibitors of cyclic AMP phosphodiesterase.

There is a continued need for developing novel PDE4 inhibitors which have a more favourable therapeutic window, i.e. fewer adverse effects, while retaining their therapeutic anti-inflammatory effect. An overview of preclinical and clinical trials with selective PDE4 inhibitors, including such inhibitors aimed for the treatment of atopic dermatitis and psoriasis, was recently given in Inflammation & Allergy: Drug Targets, 2007, 6(1), 17-26.

SUMMARY OF THE INVENTION

The inventors have surprisingly found that novel compounds of the present invention exhibit PDE4 inhibitory activity and may be useful as therapeutic agents for inflammatory allergic diseases such as bronchial asthma, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Accordingly, the present invention relates to a compound according to formula I,

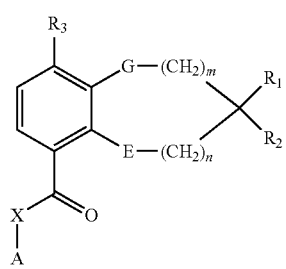

wherein m and n independently represent 0, 1, 2, 3, 4, 5, 6, or 7;
wherein G and E independently represent sulphur, oxygen, —N=, —N($R_5$)—, or —N($R_5$)C(O)—, and
$R_1$ and $R_2$, together with the carbon atom to which they are attached, form an unsaturated carbocyclic ring or a heterocyclic ring comprising one or two heteroatoms selected from oxygen, sulphur, —S(O)—, —S(O)$_2$—, —N($R_5$)—, one or more carbon atoms in said unsaturated carbocyclic ring or heterocyclic ring being optionally substituted with one or more, same or different substituents selected from $R_4$; or wherein G and E independently represent sulphur, oxygen, —N=, —N($R_5$)—, or —N($R_5$)C(O)—, and $R_1$ and $R_2$, together with the carbon atom to which they are attached, form a saturated carbocyclic ring, one or more carbon atoms in said saturated carbocyclic ring being optionally substituted with one or more, same or different substituents, selected from $R_4$, provided that when G is oxygen, m and n are not both zero and further provided that when G and E are both oxygen, the sum of m and n is six or above;

$R_3$ is halogen, hydroxy, alkyl, alkenyl, alkynyl, haloalkyl, alkoxy, haloalkoxy, alkylthio, formyl, alkoxycarbonyl, alkylcarbonyl, or aminocarbonyl;

$R_4$ is hydrogen, amino, thioxo, alkyl, haloalkyl, hydroxyalkyl, alkoxy, halogen, oxo, thia, or hydroxy;

$R_5$ is hydrogen, alkyl, haloalkyl, alkylcarbonyl, hydroxyalkyl, alkoxycarbonyl, alkylsulfonyl, alkylaminosulfonyl or aminosulfonyl;

X is a bond, —$CH_2$—, or —NH—;

A is aryl, cycloalkyl, cycloalkenyl, arylalkyl, heteroaryl, heteroarylalkyl, heterocycloalkyl or heterocycloalkenyl, optionally substituted with one or more, same or different substituents selected from $R_4$;

and pharmaceutically acceptable salts, hydrates, N-oxides or solvates thereof.

In another aspect, the invention relates to a pharmaceutical composition comprising a compound of general formula I as defined above together with a pharmaceutically acceptable vehicle or excipient or pharmaceutically acceptable carrier(s), optionally together with one or more other therapeutically active compound(s).

In yet another aspect, the invention relates to a compound according to formula I as defined above, and pharmaceutically acceptable salts, hydrates, N-oxides or solvates thereof, for use in the prophylaxis, treatment or amelioration of dermal diseases or conditions, or acute or chronic cutaneous wound disorders.

In yet another aspect, the invention relates to a method of preventing, treating or ameliorating dermal diseases or conditions, or acute or chronic cutaneous wound disorders, the method comprising administering to a person suffering from at least one of said diseases an effective amount of one or more compounds of formula I as defined above and pharmaceutically acceptable salts, hydrates, N-oxides or solvates thereof; optionally together with a pharmaceutically acceptable carrier or one or more excipients, and optionally in combination with other therapeutically active compounds.

DETAILED DESCRIPTION OF THE INVENTION

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, arylalkyl, as indicated below.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, or optionally fused bicyclic rings with 1-4 heteroatoms, and wherein at least one ring is aromatic, e.g. pyridyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

In the present context, the term "alkyl" is intended to indicate the radical obtained when one hydrogen atom is removed from a hydrocarbon. Said alkyl comprises 1-20, preferably 1-12, such as 1-6, such as 1-4 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical comprising 3-20 carbon atoms, preferably 3-10 carbon atoms, in particular 3-8 carbon atoms, such as 3-6 carbon atoms, including fused bicyclic rings, e.g. cyclopropyl, cyclobutyl, cyclopentyl, cyclohexyl, or cycloheptyl.

The term "heterocycloalkyl" is intended to indicate a cycloalkane radical as described above, wherein one or more carbon atoms are replaced by heteroatoms, comprising 1-19 carbon atoms, e.g. 2-4 carbon atoms, further comprising 1-6 heteroatoms, preferably 1, 2, or 3 heteroatoms, selected from O, N, or S, which may optionally be oxidised once or twice, e.g. [1,3]dioxole, oxetane, [1,3]dioxolane, [1,3]dioxane, tetrahydrothiopyran, tetrahydrothiopyran-1,1-dioxide, tetrahydrothiopyran-1-oxide, piperidine, tetrahydrothiophene, [1,3]-dithiane, thietane, [1,3]-dithiane-1,3-dioxide, or thietane-1-oxide, or including fused bicyclic rings with 1-4 heteroatoms, wherein at least one ring comprises a heteroatom, and wherein the other ring may for example be a carbocyclic ring, e.g. isoindolyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, propenyl, butenyl, pentenyl or hexenyl.

The term "cycloalkenyl" is intended to indicate mono-, di- tri- or tetraunsaturated non-aromatic cyclic hydrocarbonsradicals, comprising 3-20 carbon atoms, including fused bicyclic rings, typically comprising 3-10 carbon atoms, such as 3, 4, or 6 carbon atoms, e.g. cyclopropenyl, cyclobutenyl, cyclopentenyl, cyclohexenyl, cylcoheptenyl.

The term "heterocycloalkenyl" is intended to indicate a cycloalkene radical as described above, wherein one or more carbon atoms are replaced by heteroatoms, comprising 1-19 carbon atoms, e.g. 2-4 carbon atoms, further comprising 1-6 heteroatoms, preferably 1, 2, or 3 heteroatoms, selected from O, N, or S, including fused bicyclic rings with 1-4 heteroatoms, wherein at least one ring comprises a heteroatom and wherein the other ring may for example be a carbocyclic ring, e.g. dihydrofuranyl, or 2,5-dihydro-1H-pyrrolyl.

The term "arylalkyl" is intended to indicate an aryl radical as defined above covalently joined to an alkyl group, e.g. benzyl.

The term "heteroarylalkyl" is intended to indicate a heteroaryl radical as defined above covalently joined to an alkyl group.

The term "alkynyl" is intended to indicate an hydrocarbon radical comprising 1-5 triple C—C bonds and 2-20 carbon atoms, typically comprising 2-10 carbon atoms, in particular 2-6 carbon atoms, such as 2-4 carbon atoms, e.g. ethynyl, propynyl, butynyl, pentynyl or hexynyl.

The term "halogen" is intended to indicate a substituent from the $7^{th}$ main group of the periodic table, such as fluoro, chloro, bromo and iodo.

The term "haloalkyl" is intended to indicate an alkyl group as defined above substituted with one or more halogen atoms as defined above, e.g. difluoromethyl.

The term "hydroxyalkyl" is intended to indicate an alkyl group as defined above substituted with one or more hydroxy, e.g. hydroxymethyl, hydroxyethyl, hydroxypropyl.

The term "alkoxy" is intended to indicate a radical of the formula —OR', wherein R' is alkyl as indicated above, e.g. methoxy, ethoxy, n-propoxy, isopropoxy, butoxy, etc.

The term "alkoxycarbonyl" is intended to indicate a radical of the formula —C(O)—O—R', wherein R' is alkyl as indicated above, e.g. methoxycarbonyl, ethoxycarbonyl, n-propoxycarbonyl, isopropoxycarbonyl, etc.

The term "alkylcarbonyl" is intended to indicate a radical of the formula —C(O)—R', wherein R' is alkyl as indicated above, e.g. ethanoyl, acetyl.

The term "aminosulfonyl" is intended to indicate a radical of the formula —S(O)$_2$—NR", wherein R' is as indicated above, e.g. —SO$_2$Me.

The term "heterocyclic ring" is intended to include the definitions heteroaryl, heterocycloalkyl and heterocylcoalkenyl as defined above, further including annelated ring systems with each other or with cyclic hydrocarbons, e.g. 2,5-dihydrobenzo(b)dioxocine, 2,3,5,8-tetrahydro-[1,4]dioxocine, 5,8-dihydro-[1,4]dioxocine.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

EMBODIMENTS OF THE PRESENT INVENTION

In one or more embodiments of the present invention E and G are both oxygen.

In one or more embodiments of the present invention m and n are both one.

In one or more embodiments of the present invention m and n are both zero.

In one or more embodiments of the present invention $R_1$ and $R_2$, together with the carbon atom to which they are attached, form a heterocyclic ring comprising one or two heteroatoms selected from the group consisting of —O—, —S—, —S(O)—, —S(O$_2$)—, —N=, and —N(R$_5$)—; one or more carbon atoms in the heterocyclic ring being optionally substituted with one or more substituents, same or different, selected from $R_4$.

In one or more embodiments of the present invention $R_1$ and $R_2$, together with the carbon atom to which they are attached, form a heterocycloalkyl ring comprising one or two heteroatoms selected from the group consisting of —O—, —S—, —S(O)—, —S(O$_2$)—, and —N(R$_5$)—; one or more carbon atoms in the heterocycloalkyl ring being optionally substituted with one or more, same or different substituents selected from $R_4$.

In one or more embodiments of the present invention $R_1$ and $R_2$, together with the carbon atom to which they are attached, form a 4-, 5- or 6-membered heterocyclic ring, in particular a 6-membered heterocyclic ring.

In one or more embodiments of the present invention the heterocyclic ring is tetrahydropyran, oxetane, [1,3]dioxolane, [1,3]dioxane, tetrahydrothiopyran, tetrahydrothiopyran-1,1-dioxide, tetrahydrothiopyran-1-oxide, piperidine, tetrahydrothiophene, [1,3]-dithiane, thietane, [1,3]-dithiane-1,3-dioxide, thietane-1-oxide, or thiethane-1,1-dioxide In one or more embodiments of the present invention the heterocyclic ring formed of $R_1$ and $R_2$ together with the carbon atom to which they are attached comprises one heteroatom or two heteroatoms in said ring.

In one or more embodiments of the present invention the heteroatom is located in position 4 of the heterocyclic ring. The heteroatom may, for example, be O.

In one or more embodiments of the present invention the heteroatom(s) is/are oxygen, sulphur, —S(O)—, or —S(O)$_2$—.

In one or more embodiments of the present invention A represents heteroaryl or heteroarylalkyl.

In one or more embodiments of the present invention A represents pyridyl, pyrazinyl or quinolyl.

In other embodiments A may represent phenyl.

In one or more embodiments of the present invention A is substituted with halogen, in particular chlorine, fluorine, bromine or iodine.

In one or more embodiments of the present invention $R_3$ represents $C_{1-6}$ alkoxy, $C_{1-6}$halogenalkyl, or halogen.

In one or more embodiments of the present invention $R_3$ represents methoxy or ethoxy.

In one or more embodiments of the present invention X is —CH$_2$— or —NH—.

In one or more embodiments of the present invention A is 4-(3,5-dichloropyridyl).

In one or more embodiments of the present invention, the compound of formula I is represented by formula Ia or Ib

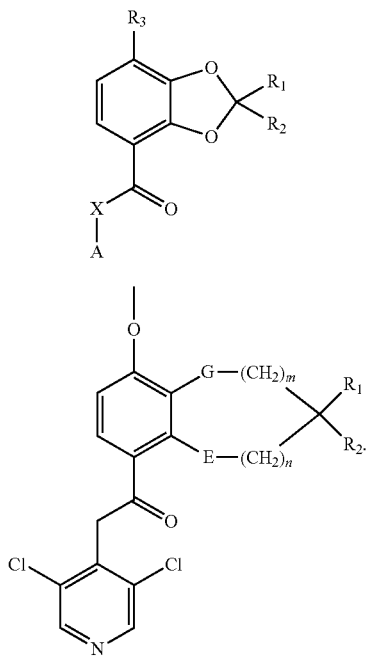

wherein X, A, G, E, $R_1$, $R_2$, $R_3$, $R_4$, $R_5$, m and n are as defined above.

In a particular embodiment of the present invention X=—NH— when $R_3$ represents $C_{1-6}$ alkoxy.

The present invention includes all embodiments wherein X, A, G, E, $R_1$, $R_2$, $R_3$, $R_4$, $R_5$ are combined in any manner described herein.

In particular compounds of formula I may be selected from one of the following compounds:

2-(3,5-Dichloropyridine-4-yl)-1-(7-methoxy-2',3',5',6'-tetrahydro-spiro[1,3-benzodioxole-2,4'-(4H)-pyran]-4-yl)ethanone (compound 101), N-(3,5-Dichloropyridine-4-yl)-7-methoxy-2',3',5',6'-tetrahydro-spiro[1,3-benzodioxole-2,4'-(4H)-pyran]-4-carboxamide (compound 102), 2-(3,5-Dichloro-1-oxido-pyridine-4-yl)-1-(7-methoxy-2',3',5',6'-tetrahydro-spiro[1,3-benzodioxole-2,4'-(4H)-pyran]-4-yl)ethanone (compound 103), 2-(3,5-Dichloropyridine-4-yl)-1-(7-methoxy-4',5'-dihydro-spiro[1,3-benzo-dioxole-2,3-(2H)-thiophen]-4-yl)ethanone (compound 104), 2-(3,5-Dichloropyridine-4-yl)-1-(7-methoxy-spiro[1,3-benzodioxole-2,4'-piperidine]-4-yl)ethanone (compound 105), 2-(3,5-Dichloropyridine-4-yl)-1-(7-methoxy-1-[methoxycarbonyl]-spiro[1,3-benzodioxole-2,4'-piperidine]-4-yl)ethanone (compound 106), 2-(3,5-Dichloropyridine-4-yl)-1-(7-methoxy-1-[methylsulfonyl]-spiro[1,3-benzodioxole-2,4'-piperidine]-4-yl)ethanone (compound 107), 2-(3,5-Dichloropyridine-4-yl)-1-(7-methoxy-1-acetyl-spiro[1,3-benzodioxole-2,4'-piperidine]-4-yl)ethanone (compound 108)

2-(3,5-Dichloropyridine-4-yl)-1-(7-methoxy-1'-methyl-spiro[1,5-benzodioxole-2,4'-piperidine]-4-yl)ethanone (compound 109), 2-(3,5-Dichloropyridine-4-yl)-1-(7-methoxy-2',3',5',6'-tetrahydro-spiro[1,3-benzodioxole-2,4'-(4H)-thiopyran]-4-yl)ethanone (compound 110), 2-(3,5-Dichloropyridine-4-yl)-1-(7-methoxy-2',3',5',6'-tetrahydro-spiro[1,3-benzodioxole-2,4'-(4H)-thiopyran 1'-oxide]-4-yl)ethanone. (compound 111), 2-(3,5-Dichloropyridine-4-yl)-1-(7-methoxy-2',3',5',6'-tetrahydro-spiro[1,3-benzodioxole-2,4'-(4H)-thiopyran-1',1'-dioxide]-4-yl)ethanone (compound 112), or 2-(3,5-Dichloro-1-oxido-pyridine-4-yl)-1-(7-methoxy-2',3',5',6'-tetrahydro-spiro[1,3-benzodioxole-2,4'-(4H)-thiopyran-1',1'-dioxide]-4-yl)ethanone (compound 113);

2-(3-bromopyridine-4-yl)-1-(7-methoxy-2',3',5',6'-tetrahydro-spiro[1,3-benzodioxole-2,4'-(4H)-thiopyran]-4-yl)ethanone (compound 114);

2-(3-Bromo-pyrazin-2-yl))-1-(7-methoxy-2',3',5',6'-tetrahydro-spiro[1,3-benzodioxole-2,4'-(4H)-thiopyran]-4-yl)ethanone (compound 115);

2-(-pyrazin-2-yl)-1-(7-methoxy-2',3',5',6'-tetrahydro-spiro[1,3-benzodioxole-2,4'-(4H)-thiopyran]-4-yl)ethanone (compound 116);

2-(-pyridin-4-yl-)-1-(7-methoxy-2',3',5',6'-tetrahydro-spiro[1,3-benzo-dioxole-2,4'-(4H)-thiopyran]-4-yl)ethanone (compound 117);

2-(quinolin-4-yl-)-1-(7-methoxy-2',3',5',6'-tetrahydro-spiro[1,3-benzo-dioxole-2,4'-(4H)-thiopyran]-4-yl)ethanone (compound 118);

2-(2,6-Dichloro-phenyl)-1-(7-methoxy-2',3',5',6'-tetrahydro-spiro[1,3-benzo-dioxole-2,4'-(4H)-thiopyran]-4-yl)ethanone (compound 119);

2-(2-Chloro-phenyl)-1-(7-methoxy-2',3',5',6'-tetrahydro-spiro[1,3-benzo-dioxole-2,4'-(4H)-thiopyran]-4-yl)ethanone (compound 120);

2-(3,5-Dichloropyridin-4-yl)-1-{9-methoxy-spiro[2H-1,5-benzodioxepin-3(4H),3'-oxetane]-6-yl}ethanone (compound 121);

2-(3,5-Dichloro-1-oxido-pyridin-4-yl)-1-{9-methoxy-spiro[2H-1,5-benzodioxepin-3(4H),3'-oxetane]-6-yl}ethanone (compound 122);

2-(3,5-Dichloropyridin-4-yl)-1-{9-methoxy-spiro[2H-1,5-benzodioxepin-3(4H),3'-thietane]-6-yl}ethanone (compound 123);

2-(3,5-Dichloropyridin-4-yl)-1-{9-methoxy-spiro[2H-1,5-benzodioxepin-3(4H),3'-thietane-1',1'-dioxide]-6-yl}ethanone (compound 124);

2-(3,5-Dichloropyridin-1-oxido-4-yl)-1-{9-methoxy-spiro[2H-1,5-benzodioxepin-3(4H),3'-thietane-1',1'-dioxide]-6-yl}ethanone (compound 125);

2-(3,5-Dichloropyridin-4-yl)-1-{9-methoxy-spiro[2H-1,5-benzodioxepin-3(4H),2'-(1,3-dioxolane)]-6-yl}ethanone (compound 126);

2-(3,5-Dichloropyridin-4-yl)-1-{9-methoxy-spiro[2H-1,5-benzodioxepin-3(4H),4'-tetrahydropyran]-6-yl}ethanone (compound 127);

2-(3,5-Dichloro-1-oxido-pyridin-4-yl)-1-{9-methoxy-spiro[2H-1,5-benzodioxepin-3(4H),4'-tetrahydropyran]-6-yl}ethanone (compound 128);

2-(3,5-Dichloropyridin-4-yl)-1-{9-methoxy-2',2'-dimethyl-spiro[2H-1,5-benzodioxepin-3(4H),5'-[1,3]dioxane]-6-yl}ethanone (compound 129);

2-(3,5-Dichloropyridin-4-yl)-1-{9-methoxy-spiro[2H-1,5-benzodioxepin-3(4H),5'-[1,3]dioxane]-6-yl}ethanone (compound 130);

2-(3,5-Dichloro-1-oxido-pyridine-4-yl)-1-{9-methoxy-spiro[2H-1,5-benzodioxepin-3(4H),5'-[1,3]dioxane]-6-yl}ethanone (compound 131); and 2-(3,5-Dichloropyridin-4-yl)-1-{9-methoxy-spiro[2H-1,5-benzodioxepin-3(4H),5'-[1,3]dithiane]-6-yl}ethanone (compound 132)

and pharmaceutically acceptable salts, hydrates, N-oxides or solvates thereof.

In one or more embodiments of the present invention, the compounds of general formula I have a molecular weight below 800 Dalton, such as below 750 Dalton, e.g. below 700 Dalton, or below 650, 600, 550, or 500 Dalton.

In one or more embodiments of the present invention, the compounds of formula I as defined above are useful in therapy.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as 1-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the invention, optionally in combination with other active compounds, may be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practicing physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily doses is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose capable of being administered topically to a patient in an application per square centimeter of the infected area of from 0.1 mg to 10 mg, and preferably from 0.2 mg to 1 mg, of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, $9^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by any of the methods well known in the art of pharmacy, e.g. as disclosed in Remington, *The Science and Practice of Pharmacy*, $20^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, sprays, foams, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts, salicylazosulfapyridine and calcineurin inhibitors.

The invention is described in further detail in the following examples which are not in any way intended to limit the scope of the invention as claimed.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known compounds which are commercially available, or they may be prepared by routine synthetic methods well known to a person skilled in the art.

The compounds of the present invention or any intermediate may be purified if required using standard methods well known to a synthetic organist chemist, e.g. methods described in "Purification of Laboratory Chemicals", $5^{th}$ ed. 2003.

Starting materials are either known compounds, commercially available, or they may be prepared by routine synthetic methods well known to a person skilled in the art.

GENERAL PROCEDURES, PREPARATIONS AND EXAMPLES $^1$H nuclear magnetic resonance (NMR) spectra were recorded at 300 MHz and $^{13}$C NMR spectra at 75.6 MHz. Chemical shift values (δ, in ppm) are quoted in the specified solvent relative to internal tetramethylsilane (δ=0.00) or chloroform (δ=7.25) or deuteriochloroform (δ=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0.063 mm). The solvent ratios indicated refer to v:v unless otherwise noted.

The following abbreviations have been used throughout:
DCM dichloromethane
DMF N,N'-Dimethylformamide
DMSO dimethyl sulfoxide
Et ethyl
EtOAc ethyl acetate
h hour
L liter
LDA lithium diisopropylamide
LiHMDS lithium Hexamethyldisilazide
m milli
Me methyl
MeOH methanol
NMR nuclear magnetic resonance
ppt precipitate
rt room temperature
TsCl p-toluenesulphonyl chloride
THF tetrahydrofuran
v volume
Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 μm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

Analytical HPLC/MS

Method A: Analytical HPLC/MS was performed on a Dionex APS-system with a P680A analytical pump and a Thermo MSQ Plus mass spectrometer. Column: Waters XTerra C-18, 150 mm×4.6 mm, 5 μm; solventsystem: A=water (0.1% formic acid) and B=acetonitrile (0.1% formic acid); flow rate=1.0 mL/min; method (10 min): Linear gradient method going from 10% B to 100% B in 6.6 minutes and staying at 100% B for another 1.5 minutes.

Method B: Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 μm; solventsystem: A=water:acetonitrile 95:5 (0.05% formic acid) and B=acetonitrile (0.05% formic acid); flow rate=1.0 mL/min; method (8 min): Linear gradient method going from 10% B to 100% B in 6.0 minutes and staying at 100% B for 1 minute.

General Procedure of Preparation:

The compounds of the invention can for example be prepared by the following general methods:

Compounds of the general formula Ia, wherein $R_1$, $R_2$, and $R_3$ are as defined above, can be prepared as follows:

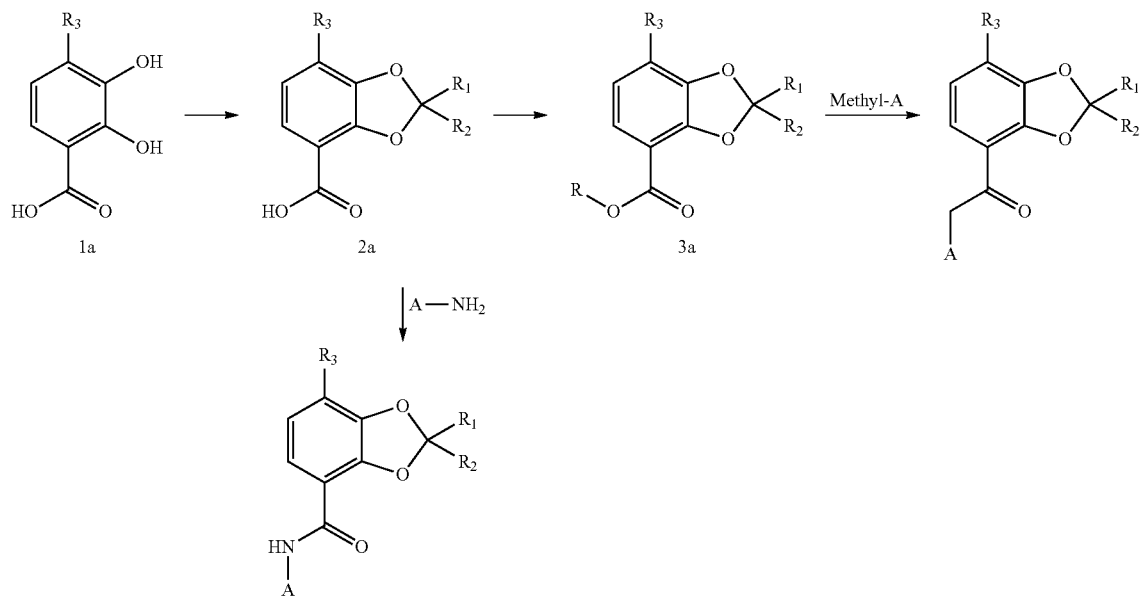

Starting materials of formula is are prepared according to standard procedures known to chemist skilled in the art. 2,3,4-trimethoxy benzoic acid is selectively di-demethylated at the 2- and 3-position using $BCl_3$ according to Kaisalo et al. Synth. Commun., (1986), 16, 645-48.

Subsequent reaction of the deprotected compound in neat ketones, enol ethers, ketals or a mixture of these with or without additional catalysts such as para-toluenesulfonic acid or a lewis acid at temperature from room temperature to 180° C. using either microwave or conventional heating, results in the compounds 2a.

Reaction of compounds with formula 2a with MeI (or dimethyl sulphate) in the presence of a suitable base, such as $K_2CO_3$ $KHCO_3$ or $Et_3N$ in a suitable solvent such as DMF, acetone, THF or DCM at temperatures from room temperature to 100° C. give compounds of the formula 3a.

The ester 3a may also be prepared by classical esterification methods using the alcohol and a suitable acid e.g. $H_2SO_4$.

Compounds of the formula Ia (X=CH$_2$) were obtained by condensation of the generated methyl ester with lithio carbanions generated from A-Methyl, wherein A is defined as described above, and a suitable base, such as LDA or LiHMDS in a suitable solvent such as THF at temperatures from minus 78° C. to room temperature. Alternatively to the lithio carbanions a grignard reagent may be used.

Compounds of the formula Ia (X=NH) were obtained by reaction of compounds with the formula 2a with (COCl)$_2$, SOCl$_2$ or PCl$_5$ in a suitable solvent such as DCM or toluene with or without catalytic amount of DMF at temperatures from 0° C. to 70° C. to afford the corresponding acid chloride. After evaporation of the solvent in vacuo subsequent condensation of the generated acid chloride with nitrogen-anions, generated by addition a suitable base, such as NaH, LDA or LiHMDS in a suitable solvent such as THF at temperatures from minus 78° C. to room temperature to A-NH$_2$, wherein A is defined as described above, are performed.

Compounds of the general formular Ib, wherein R$_1$, R$_2$, and R$_3$ are as defined above, can be prepared as follows:

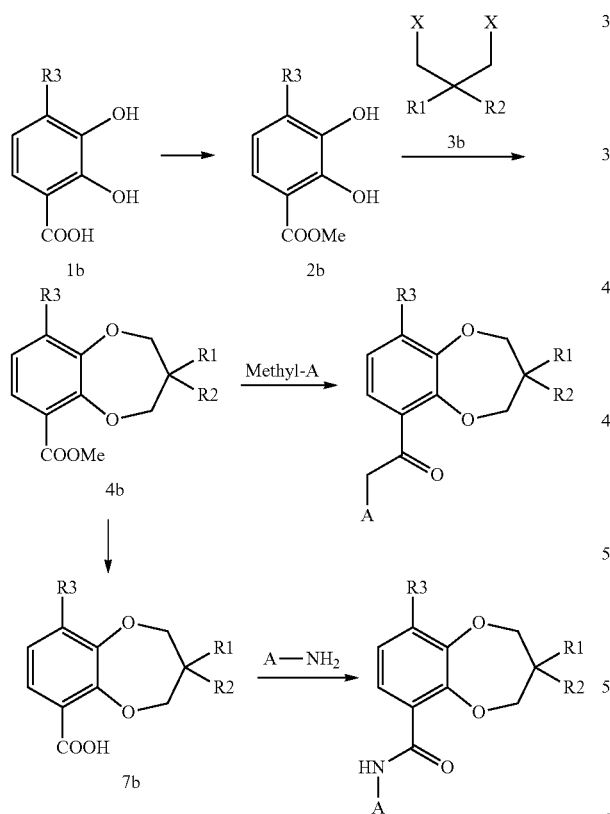

Esterification of 1b using standard procedures, e.g. MeOH and H$_2$SO$_4$ results in the ester 2b.

Alkylation of 2b using 3b (X=Br, I, OTs) in the presence of a suitable base, such as K$_2$CO$_3$ in a suitable solvent such as DMSO at temperatures from room temperature to 120° C. give compounds of the formula 4b.

Compounds of the formula Ib (X=CH$_2$) were obtained by condensation of the generated methyl ester with lithio carbanions generated from A-Methyl, wherein A is defined as described above, and a suitable base, such as LDA or LiHMDS in a suitable solvent such as THF at temperatures from minus 78° C. to room temperature. Alternatively to the lithio carbanions a grignard reagent may be used.

Esther hydrolysis using standard conditions (acidic or basic) is expected to result in the carboxylic acid 7b, that can be converted to the carboxylic acid chloride and subsequently reacted with reacted with nitrogen-anions (generated from A-NH2) as described for the synthesis of Ia (X=NH.

Preparation 1

7-Methoxy-2',3',5',6'-tetrahydro-spiro[1,3-benzodioxole-2,4'-(4H)-pyran]-4-carboxylic acid (compound 501)

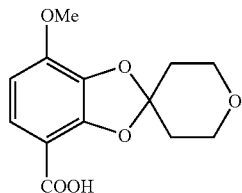

A suspension of 2,3-dihydroxy-4-methoxybenzoic acid (6.04 g, 32.8 mmol) in 5,6-dihydro-4-methoxy-2H-pyran (20 mL, 152 mmol) was kept at 140° C. for three days. At room temperature ethyl acetate (200 mL) was added and the organic phase was extracted with saturated aqueous NaHCO$_3$ (2×50 mL). The aqueous phase was washed with Et$_2$O (2×40 mL), acidified to pH=1 with concentrated HCl and extracted with dichloromethane (2×50 mL). The organic phase was dried over MgSO$_4$. Evaporation under reduced pressure afforded traces of 2,3-dihydroxy-4-methoxybenzoic acid along with 7-methoxy-2',3',5',6'-tetrahydro-Spiro[1,3-benzodioxole-2,4'-(4H)-pyran]-4-carboxylic acid (1.23 g, 14%).
$^{13}$C NMR (DMSO) δ 164.9, 148.2, 146.6, 134.5, 123.7, 117.0, 107.1, 106.8, 64.4, 56.0, 35.3.

Preparation 2

Methyl 7-methoxy-2',3',5',6'-tetrahydro-spiro[1,3-benzodioxole-2,4'-(4H)-pyran]-4-carboxylate (compound 502)

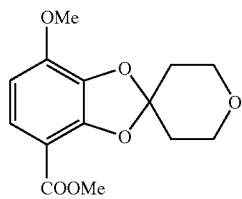

A suspension of the crude 7-methoxy-2',3',5',6'-tetrahydro-spiro[1,3-benzodioxole-2,4'-(4H)-pyran]-4-carboxylic acid (2.17 g, 8.15 mmol), KHCO$_3$ (2.58 g, 26.0 mmol) and dimethyl sulphate (1.58 mL, 16.7 mmol) in acetone (62 mL) was stirred at room temperature for two days before it was evaporated to dryness under reduced pressure. Ethyl acetate (100 mL) was added. The organic phase was washed with 0.5 M aqueous NaOH (6×30 mL) and evaporated to dryness under reduced pressure. The crude product was redissolved in dichloromethane (75 mL), dried over MgSO$_4$ and evaporated to dryness under reduced pressure. Standard silica gel column chromatography afforded methyl 7-methoxy-2',3',5',6'-tetrahydro-spiro[1,3-benzodioxole-2,4'-(4H)-pyran]-4-carboxylate (1.87 g, 79%). $^{13}$C NMR (CDCl$_3$) δ 164.9, 149.1, 147.2, 135.2, 124.0, 117.5, 107.1, 106.5, 65.2, 56.4, 51.8, 35.9.

Standard Procedure A

Example 1

2-(3,5-Dichloropyridine-4-yl)-1-(7-methoxy-2',3',5',6'-tetrahydro-spiro[1,3-benzodioxole-2,4'-(4H)-pyran]-4-yl)ethanone (compound 101)

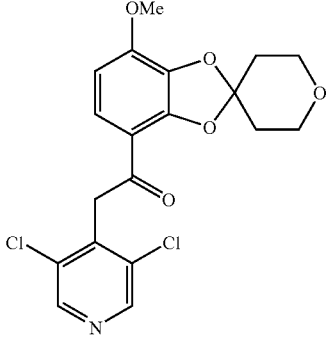

A solution of methyl 7-methoxy-2',3',5',6'-tetrahydro-spiro[1,3-benzodioxole-2,4'-(4H)-pyran]-4-carboxylate (1.80 g, 6.42 mmol) and 3,5-dichloro-4-picoline (1.46 g, 8.99 mmol) in tetrahydrofuran (33 mL) was cooled to 0° C. A 1.0 M solution of lithium bis(trimethylsilyl)amide in tetrahydrofuran (19.3 mL, 19.3 mmol) was added and the reaction mixture was allowed to reach room temperature overnight. Saturated aqueous NH$_4$Cl (70 mL) was added. The aqueous phase was extracted with dichloromethane (3×100 mL). The combined organic phase was washed with water (50 mL), dried over MgSO$_4$ and evaporated to dryness under reduced pressure. Standard silica gel column chromatography followed by recrystallization from isopropanol afforded 2-(3,5-dichloropyridine-4-yl)-1-(7-methoxy-2',3',5',6'-tetrahydro-spiro[1,3-benzodioxole-2,4'-(4H)-pyran]-4-yl)ethanone (1.90 g, 71%). $^{13}$C NMR (DMSO) δ 189.1, 148.2, 147.7, 147.0, 141.2, 134.5, 132.8, 122.0, 118.0, 113.0, 107.8, 64.4, 56.3, 43.5, 35.2.

Example 2

N-(3,5-Dichloropyridine-4-yl)-7-methoxy-2',3',5',6'-tetrahydro-spiro[1,3-benzodioxole-2,4'-(4H)-pyran]-4-carboxamide (compound 102)

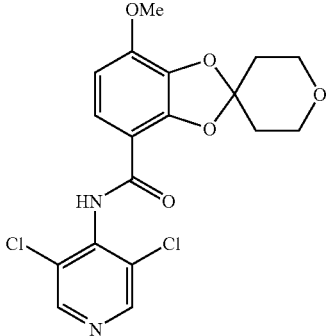

Oxalyl chloride (92 µL, 1.1 mmol) and a catalytic amount of N,N-dimethylformamide was added to a suspension of 7-methoxy-2',3',5',6'-tetrahydro-spiro[1,3-benzodioxole-2,4'-(4H)-pyran]-4-carboxylic acid (48 mg, 0.18 mmol) in dichloromethane (2 mL). After stirring for one hour at room temperature, the solvent was removed under reduced pressure and the crude acid chloride was redissolved in tetrahydrofuran (2 mL). A suspension of 3,5-dichloropyridin-4-amine (67 mg, 0.40 mmol) and NaH (a 60% dispersion in mineral oil, 16 mg, 0.40 mmol) in tetrahydrofuran (1 mL) was stirred for three hours at room temperature before it was added dropwise at room temperature to the tetrahydrofuran solution containing the crude acid chloride. After having stirred overnight at room temperature the reaction mixture was diluted with diethyl ether (30 mL) and the organic phase was washed with 0.5 M aqueous NaOH (3×10 mL). The organic phase was dried over MgSO$_4$ and evaporated to dryness under reduced pressure. Standard HPLC purification afforded N-(3,5-dichloropyridine-4-yl)-7-methoxy-2',3',6'-tetrahydro-spiro[1,3-benzodioxole-2,4'-(4H)-pyran]-4-carboxamide (14 mg, 19%). $^{13}$C NMR (DMSO) δ 160.8, 148.0, 146.5, 146.2, 141.1, 134.1, 130.5, 122.5, 118.2, 108.3, 107.6, 64.2, 56.2, 35.2.

Example 3

2-(3,5-Dichloro-1-oxido-pyridine-4-yl)-1-(7-methoxy-2',5',6'-tetrahydro-spiro[1,3-benzodioxole-2,4'-(4H)-pyran]-4-yl)ethanone (compound 103)

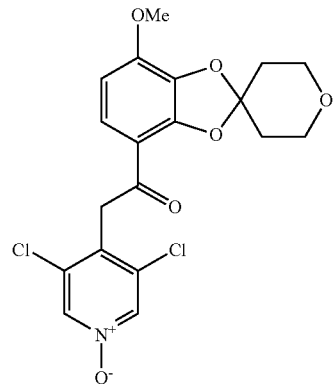

To a solution of 2-(3,5-dichloropyridine-4-yl)-1-(7-methoxy-2',3',5',6'-tetrahydro-spiro[1,3-benzodioxole-2,4'-(4H)-pyran]-4-yl)ethanone (41 mg, 0.99 mmol) in dichloromethane (0.5 mL) was added 30% H$_2$O$_2$ (25 µL) and methyltrioxorhenium(VII) (3 mg). The mixture was stirred at room temperature overnight, added MnO$_2$ (3 mg) and was stirred for another hour. Water (10 mL) was added and the aqueous phase was extracted with dichloromethane (3×10 mL). The combined organic phase was dried over MgSO$_4$ and evaporated to dryness under reduced pressure. Standard HPLC purification afforded compound 103 (8 mg, 19%). LC/MS (METHOD B): (m/z) 426.1; 428.1 (MH+); RT=2.98 min; purity (UV)=100%

Preparation 3

Tetrahydro-3,3-dimethoxythiophen (compound 503)

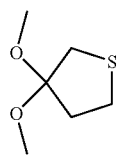

A solution of tetrahydrothiophen-3-one (10.0 g, 97.9 mmol), methyl orthoformate (21.4 mL, 196 mmol) and para-toluenesulfonic acid monohydrate (50 mg, 0.29 mmol) in dry methanol (25 mL) was refluxed for one hour. Then 1.0 M methanolic NaOMe (0.30 mL, 0.30 mmol) was added and excess of methanol and trimethyl orthoformate was removed by distillation (atmospheric pressure). Further distillation under reduced pressure afforded a mixture of tetrahydrothiophen-3-one (~0.67 g, 7%) and tetrahydro-3,3-dimethoxythiophen (~9.8 g, 67%). $^{13}$C NMR (MeOH) δ 113.01, 50.11, 36.90, 36.11, 27.72.

Preparation 4

7-Methoxy-4',5'-dihydro-spiro[1,3-benzodioxole-2,3'-(2H)-thiophen]-4-carboxylic acid (compound 504)

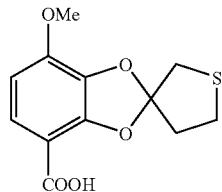

P-toluenesulfonic acid (54 mg, 0.28 mmol) was added to the mixture of tetrahydro-3,3-dimethoxythiophen (~9.8 g, 66 mmol) and tetrahydrothiophen-3-one (~0.67 g, 6.6 mmol). The oil bath was heated to 145° C. and approximately one equivalent of methanol (2.7 mL, 67 mmol) was distilled off. The temperature was lowered and distillation under reduced pressure afforded 7.04 g of an oil to which 2,3-dihydroxy-4-methoxybenzoic acid (1.00 g, 5.43 mmol) was added. The suspension was exposed to microwave heating (180° C., one hour) in a sealed reaction vessel. Filtration and subsequent standard HPLC purification afforded compound 504 (164 mg, 11%). LC/MS (METHOD B): (m/z) 267.2 (M−1); RT=2.79 min; purity (UV)=100%

Preparation 5

Methyl 7-methoxy-4',5'-dihydro-spiro[1,3-benzo-dioxole-2,3'-(2H)-thiophen]-4-carboxylate (compound 505)

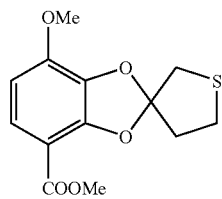

A suspension of 7-methoxy-4',5'-dihydro-spiro[1,3-benzodioxole-2,3'-(2H)-thiophen]-4-carboxylic acid (161 mg, 0.600 mmol), K$_2$CO$_3$ (166 g, 1.20 mmol) and dimethyl sulphate (74 μL, 0.78 mmol) in acetone (1 mL) was kept at 50° C. overnight. At room temperature water (15 mL) was added and the aqueous phase was extracted with ethyl acetate (2×20 mL). The organic phase was dried over MgSO$_4$ and evaporated to dryness under reduced pressure. Standard HPLC purification afforded compound 505 (24 mg, 14%). $^1$H NMR (CDCl$_3$) δ 7.44 (d, 1H), 6.56 (d, 1H), 3.94 (s, 3H), 3.88 (s, 3H), 3.32 (d, 1H), 3.24 (d, 1H), 3.05 (t, 2H), 2.49 (td, 2H).

Example 4

2-(3,5-Dichloropyridine-4-yl)-1-(7-methoxy-4',5'-dihydro-spiro[1,3-benzo-dioxole-2,3'-(2H)-thiophen]-4-yl)ethanone (compound 104)

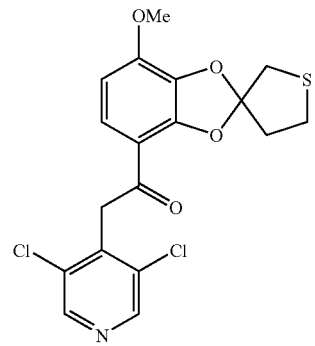

A solution of methyl 7-methoxy-4',5'-dihydro-spiro[1,3-benzodioxole-2,3'-(2H)-thiophen]-4-carboxylate (24 mg, 85 μmol) and 3,5-dichloro-4-picoline (21 mg, 0.13 mmol) in tetrahydrofuran (1 mL) was cooled to 0° C. A 1.0 M solution of lithium bis(trimethylsilyl)amide in tetrahydrofuran (0.26 mL, 0.26 mmol) was added and the reaction mixture was allowed to reach room temperature overnight. Saturated aqueous NH$_4$Cl (10 mL) was added. The aqueous phase was extracted with dichloromethane (3×10 mL). The combined organic phase was washed with water (20 mL), dried over MgSO$_4$ and evaporated to dryness under reduced pressure. Standard HPLC purification afforded the title compound (12 mg, 34%). $^{13}$C NMR (DMSO) δ189.02, 148.09, 147.51, 147.05, 140.98, 134.48, 132.69, 127.57, 122.31, 112.81, 107.81, 56.35, 43.26, 37.54, 36.54, 25.70.

Preparation 6

1-Acetyl-4,4-dimethoxy-piperidine (compound 506)

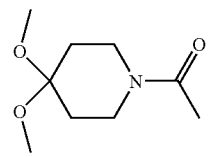

A solution of 1-acetyl-4-piperidone (17.0 g, 121 mmol), trimethyl orthoformate (26.4 mL, 241 mmol) and para-toluenesulfonic acid monohydrate (80 mg, 0.42 mmol) in dry methanol (34 mL) was refluxed for one hour. Then 1.0 M methanolic NaOMe (0.42 mL, 0.42 mmol) and excess of methanol and trimethyl orthoformate were removed by distillation (atmospheric pressure). Further distillation under reduced pressure afforded 1-acetyl-4,4-dimethoxy-piperidine (20.2 g, 89%) $^1$H NMR (DMSO) δ 3.45-3.32 (m, 4H), 3.10 (s, 6H), 1.99 (s, 3H), 1.72-1.62 (m, 2H), 1.61-1.52 (m, 2H).

Preparation 7

1-Acetyl-1,2,3,6-tetrahydro-4-methoxy-pyridine (compound 507)

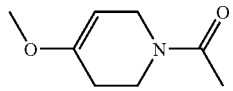

To 1-acetyl-4,4-dimethoxy-piperidine (20.2 g, 108 mmol) was added para-toluenesulfonic acid monohydrate (80 mg, 0.42 mmol). The mixture was heated to 160° C. and approximately one equivalent of methanol (4.38 mL, 108 mmol) was distilled off. The temperature was lowered and distillation under reduced pressure afforded a mixture of 1-acetyl-4,4-dimethoxy-piperidine (1.4 g, 7%) and 1-acetyl-1,2,3,6-tetrahydro-4-methoxy-pyridine (14.2 g, 85%). $^1$H NMR (DMSO) δ 4.68-4.62 (m, 1H), 4.00-3.88 (m, 2H), 3.59-3.49 (m, 2H), 3.49-3.45 (m, 3H), 2.19-2.12 (m, 1H), 2.09-2.03 (m, 1H), 2.03-1.96 (m, 3H).

Preparation 8

7-Methoxy-1'-acetyl-spiro[1,3-benzodioxole-2,4'-piperidine]-4-carboxylic acid (compound 508)

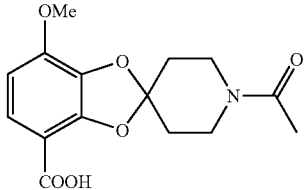

A mixture of 2,3-dihydroxy-4-methoxybenzoic acid (1.23 g, 6.67 mmol), 1-acetyl-4,4-dimethoxy-piperidine (1.4 g, 7.6 mmol) and 1-acetyl-1,2,3,6-tetrahydro-4-methoxy-pyridine (14.2 g, 91.5 mmol) was exposed to microwave heating (180° C., one hour) in a sealed reaction vessel. Filtration and subsequent standard HPLC purification afforded compound 508 (0.54 g, 26%). LC/MS (METHOD B): (m/z) 308.2 (MH+); RT=2.27 min; purity (UV)=95%.

Preparation 9

Methyl 7-methoxy-spiro[1,3-benzodioxole-2,4'-piperidine]-4-carboxylate (compound 509)

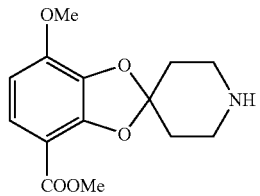

A solution of 7-methoxy-1'-acetyl-spiro[1,3-benzodioxole-2,4'-piperidine]-4-carboxylic acid (143 mg, 0.467 mmol) and LiOH (224 mg, 9.34 mmol) in water (3 mL) and MeOH (3 mL) was heated to 75° C. for five hours. At room temperature the mixture was neutralized with 2M HCl and evaporated to dryness under reduced pressure. The crude 7-methoxy-spiro[1,3-benzodioxole-2,4'-piperidine]-4-carboxylic acid [LC/MS (METHOD B): (m/z) 266.2 (MH+); RT=1.57 min; purity (UV)=82%] was refluxed overnight in 1.7 M methanolic HCl (5 mL). At room temperature water (20 mL) was added. The aqueous phase was washed with Et$_2$O (10 mL), made basic by addition of Na$_2$CO$_3$ and extracted with dichloromethane (3×10 mL). The organic phase was dried over MgSO$_4$ and evaporation under reduced pressure afforded methyl 7-methoxy-spiro[1,3-benzodioxole-2,4'-piperidine]-4-carboxylate (75 mg, 57%). $^1$H NMR (DMSO) δ 7.31 (d, 1H), 6.72 (d, 1H), 3.87 (s, 3H), 3.78 (s, 3H), 2.96-2.77 (m, 4H), 1.94-1.83 (m, 4H).

Example 5

2-(3,5-Dichloropyridine-4-yl)-1-(7-methoxy-spiro[1,3-benzodioxole-2,4'-piperidine]-4-yl)ethanone (compound 105)

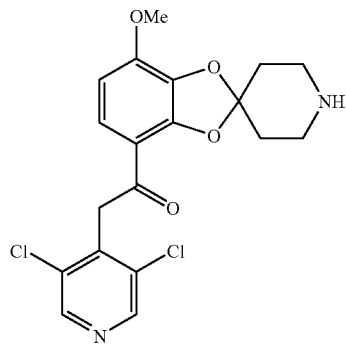

A solution of methyl 7-methoxy-spiro[1,3-benzodioxole-2,4'-piperidine]-4-carboxylate (75 mg, 0.268 mol) and 3,5-dichloro-4-picoline (65 mg, 0.40 mmol) in tetrahydrofuran (2.5 mL) was cooled to 0° C. A 1.0 M solution of lithium bis(trimethylsilyl)amide in tetrahydrofuran (0.80 mL, 0.80 mmol) was added and the reaction mixture was allowed to reach room temperature overnight. Saturated aqueous NH$_4$Cl (10 mL) was added. The aqueous phase was extracted with dichloromethane (3×10 mL). The combined organic phase was dried over MgSO$_4$ and evaporated to dryness under reduced pressure. Standard HPLC purification afforded compound 105 (58 mg, 53%). $^1$H NMR (DMSO) δ 8.66 (s, 2H), 7.38-7.36 (m, 1H), 6.83-6.80 (m, 1H), 4.62 (s, 2H), 3.91 (s, 3H), 3.02-2.91 (m, 4H), 2.12-1.93 (m, 4H).

Example 6

2-(3,5-Dichloropyridine-4-yl)-1-(7-methoxy-1'-[methoxycarbonyl]-spiro[1,3-benzodioxole-2,4'-piperidine]-4-yl)ethanone (compound 106)

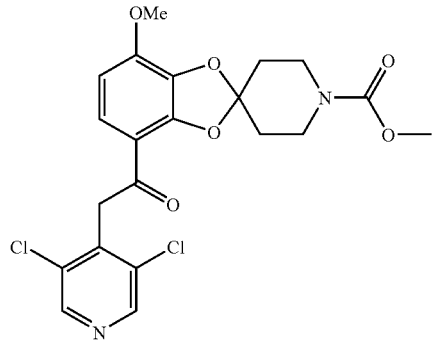

A solution of 2-(3,5-dichloropyridine-4-yl)-1-(7-methoxy-spiro[1,3-benzo-dioxole-2,4'-piperidine]-4-yl)ethanone (10 mg, 24 μmol), triethylamine (24 μL, 171 μmol) and methyl chloroformate (104, 122 μmol) in dichloromethane (200 μL) was kept at room temperature overnight. Water (500 μL) was added and the aqueous phase extracted with dichloromethane (3×500 μL). The organic phase was dried over MgSO$_4$ and evaporated to dryness under reduced pressure. Standard HPLC purification afforded compound 106 (2.5 mg, 22%). $^1$H NMR (DMSO) δ 8.65 (s, 2H), 7.39 (d, 1H), 6.84 (d, 1H), 4.62 (s, 2H), 3.91 (s, 3H), 3.80-3.66 (m, 2H), 3.62 (s, 3H), 3.58-3.46 (m, 2H), 2.18-1.97 (m, 4H).

Example 7

2-(3,5-Dichloropyridine-4-yl)-1-(7-methoxy-1'-[methylsulfonyl]-spiro[1,3-benzodioxole-2,4'-piperidine]-4-yl)ethanone (compound 107)

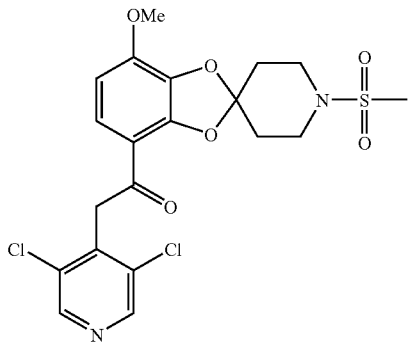

A solution of 2-(3,5-dichloropyridine-4-yl)-1-(7-methoxy-spiro[1,3-benzo-dioxole-2,4'-piperidine]-4-yl)ethanone (10 mg, 24 mmol), triethylamine (24 μL, 171 mmol) and mesyl chloride (10 μL, 122 μmol) in dichloromethane (200 μL) was kept at room temperature overnight. Water (500 μL) was added and the aqueous phase extracted with dichloromethane (3×500 μL). The organic phase was dried over MgSO$_4$ and evaporated to dryness under reduced pressure. Standard HPLC purification afforded compound 107 (1.8 mg, 15%). $^1$H NMR (DMSO) δ 8.66 (s, 2H), 7.45-7.38 (m, 1H), 6.88-6.81 (m, 1H), 4.62 (s, 2H), 3.92 (s, 3H), 3.50-3.36 (m, 4H), 2.98 (s, 3H), 2.29-2.11 (m, 4H).

Example 8

2-(3,5-Dichloropyridine-4-yl)-1-(7-methoxy-1'-acetyl-spiro[1,3-benzodioxole-2,4'-piperidine]-4-yl)ethanone (compound 108)

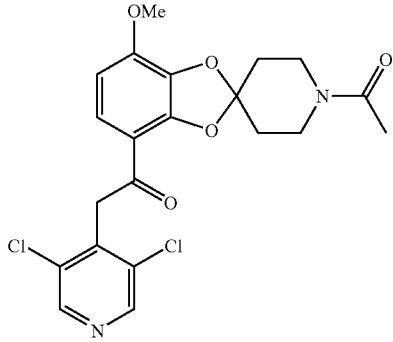

A solution of 2-(3,5-dichloropyridine-4-yl)-1-(7-methoxy-spiro[1,3-benzo-dioxole-2,4'-piperidine]-4-yl)ethanone (10 mg, 24 μmol), triethylamine (24 μL, 171 μmol) and acetic anhydride (12 μL, 122 μmol) in dichloromethane (200 μL) was kept at room temperature overnight. Water (500 μL) was added and the aqueous phase extracted with dichloromethane (3×500 μL). The organic phase was dried over MgSO$_4$ and evaporated to dryness under reduced pressure. Standard HPLC purification afforded compound 108 (7.2 mg, 65%). $^1$H NMR (DMSO) δ 8.66 (s, 2H), 7.40 (d, 1H), 6.84 (d, 1H), 4.63 (s, 2H), 3.92 (s, 3H), 3.90-3.84 (m, 1H), 3.75-3.68 (m, 1H), 3.64-3.58 (m, 1H), 3.55-3.49 (m, 1H), 2.21-2.15 (m, 1H), 2.15-2.05 (m, 5H), 2.01-1.94 (m, 1H).

Preparation 10

4,4-Dimethoxytetrahydro-(4H)-thiopyran (compound 510)

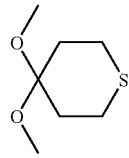

A mixture of tetrahydro-(4H)-thiopyran-4-one (15.0 g, 129 mmol), trimethyl orthoformate (28.3 mL, 258 mmol) and para-toluenesulfonic acid monohydrate (67 mg, 0.35 mmol) in methanol (40 mL) was refluxed for 1 hour. The reaction mixture was cooled to room temperature, 1 M NaOMe (0.35 mL, 0.35 mmol) was added and excess methanol and trimethyl orthoformate was removed by distillation (atmospheric pressure). Further distillation under reduced pressure afforded 4,4-dimethoxytetrahydro-(4H)-thiopyran (20.7 g, 99%). $^1$H NMR (DMSO) δ 3.07 (s, 6H), 2.56 (m, 4H), 1.84 (m, 4H).

Preparation 11

7-Methoxy-2',3',5',6'-tetrahydro-spiro[1,3-benzodioxole-2,4'-(4H)-thiopyran]-4-carboxylic acid (compound 511)

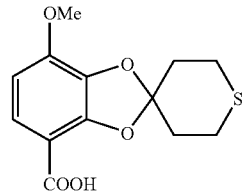

P-Toluenesulfonic acid (97 mg, 0.51 mmol) was added to 4,4-dimethoxytetrahydro-(4H)-thiopyran (20.7 g, 128 mmol) and the mixture was heated to 145° C. and kept at that temperature until approximately one equivalent of methanol (5.17 mL, 128 mmol) was distilled off. The mixture was then cooled to 130° C. and distillation under reduced pressure afforded 10.1 g of a 5:3 mixture of 5,6-dihydro-4-methoxy-(2H)-thiopyran [$^1$H NMR (DMSO) δ 4.87 (m, 1H), 3.44 (s, 3H), 3.15 (dt, 2H), 2.72 (t, 2H), 2.22 (m, 2H)] and 4,4-dimethoxytetrahydro-(4H)-thiopyran. Without further purification the mixture was added to 2,3-dihydroxy-4-methoxybenzoic acid (2.00 g, 10.9 mmol) and the suspension was exposed to microwave heating (180° C., one hour) in a sealed reaction vessel. Ethyl acetate (100 mL) was added and the organic phase was first washed with 0.5 M HCl (40 mL) and then extracted with saturated aqueous NaHCO$_3$ (2×30 mL).

The aqueous phase was washed with Et$_2$O (2×40 mL), acidified to pH=1 with concentrated HCl and extracted with dichloromethane (2×30 mL). The organic phase was dried over MgSO$_4$. Evaporation under reduced pressure afforded 7-methoxy-2',3',5',6'-tetrahydro-spiro[1,3-benzodioxole-2,4'-(4H)-thiopyran]-4-carboxylic acid (1.86 g, 61%). $^{13}$C NMR (DMSO) δ 164.9, 148.2, 146.6, 134.5, 123.8, 118.0, 107.2, 106.9, 56.1, 35.9, 25.4.

Preparation 12

Methyl 7-methoxy-2',3',5',6'-tetrahydro-spiro[1,3-benzodioxole-2,4'-(4H)-thiopyran]-4-carboxylate (compound 512)

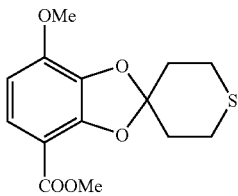

A suspension of 7-methoxy-2',3',5',6'-tetrahydro-spiro[1,3-benzodioxole-2,4'-(4H)-thiopyran]-4-carboxylic acid (570 mg, 2.02 mmol), K$_2$CO$_3$ (558 mg, 4.04 mmol) and dimethyl sulphate (0.25 mL, 2.62 mmol) in acetone (14 mL) was stirred at 50° C. overnight. At room temperature water (30 mL) was added. The aqueous phase was extracted with dichloromethane (3×15 mL). The combined organic phase was dried over MgSO$_4$ and evaporated to dryness under reduced pressure. Standard silica gel column chromatography afforded methyl 7-methoxy-2',3',5',6'-tetrahydro-spiro[1,3-benzodioxole-2,4'-(4H)-thiopyran]-4-carboxylate (407 mg, 68%). $^{13}$C NMR (DMSO) δ 163.8, 148.1, 146.9, 134.6, 123.4, 118.3, 107.1, 105.9, 56.1, 51.6, 35.9, 25.4.

Example 9

2-(3,5-Dichloropyridine-4-yl)-1-(7-methoxy-2',3',5',6'-tetrahydro-spiro[1,3-benzodioxole-2,4'-(4H)-thiopyran]-4-yl)ethanone (compound 110)

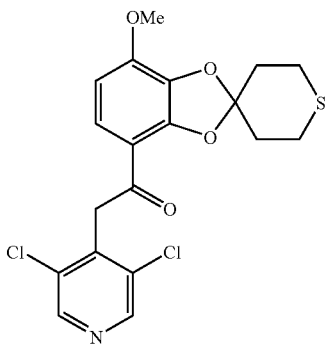

A solution of methyl 7-methoxy-2',3',5',6'-tetrahydro-spiro[1,3-benzodioxole-2,4'-(4H)-thiopyran]-4-carboxylate (40 mg, 0.14 mmol) and 3,5-dichloro-4-picoline (33 mg, 0.20 mmol) in tetrahydrofuran (1.1 mL) was cooled to 0° C. A 1.0 M solution of lithium bis(trimethylsilyl)amide in tetrahydrofuran (0.41 mL, 0.41 mmol) was added and the reaction mixture was allowed to reach room temperature overnight. Saturated aqueous NH$_4$Cl (20 mL) was added. The aqueous phase was extracted with dichloromethane (3×15 mL). The combined organic phase was dried over MgSO$_4$ and evaporated to dryness under reduced pressure. Standard HPLC purification afforded 2-(3,5-dichloropyridine-4-yl)-1-(7-methoxy-2',3',5',6'-tetrahydro-spiro[1,3-benzodioxole-2,4'-(4H)-thiopyran]-4-yl)ethanone (38 mg, 67%). $^{13}$C NMR (DMSO) δ 189.1, 148.2, 147.7, 147.0, 141.3, 134.5, 132.8, 122.0, 119.1, 113.0, 107.9, 56.3, 43.6, 35.9, 25.5.

Example 10

2-(3,5-Dichloropyridine-4-yl)-1-(7-methoxy-2',3',5',6'-tetrahydro-spiro[1,3-benzodioxole-2,4'-(4H)-thiopyran 1'-oxide]-4-yl)ethanone (compound 111)

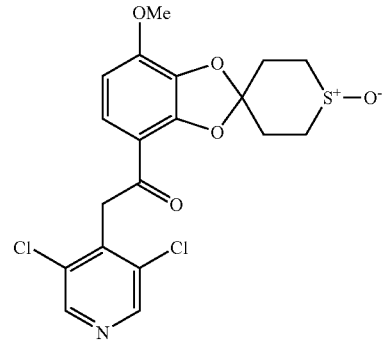

To a solution of 2-(3,5-dichloropyridine-4-yl)-1-(7-methoxy-2',3',5',6'-tetrahydro-spiro[1,3-benzodioxole-2,4'-(4H)-thiopyran]-4-yl)ethanone (17 mg, 40 mmol) in dichloromethane (0.5 mL) was added first 0.25 M H$_2$O$_2$ in ethanol (128 μL, 32 mmol) and then secondly methyltrioxorhenium (VII) (1 mg, 4 mmol). The mixture was stirred at room temperature for two days and evaporated to dryness under reduced pressure. Standard HPLC purification afforded 2-(3,5-dichloropyridine-4-yl)-1-(7-methoxy-2',3',5',6'-tetrahydro-spiro[1,3-benzo-dioxole-2,4'-(4H)-thiopyran 1'-oxide]-4-yl)ethanone (7 mg, 40%). $^1$H NMR (DMSO) δ 8.66 (s, 2H), 7.42 (d, 1H), 6.85 (d, 1H), 4.63 (s, 2H), 3.93 (s, 3H), 3.17-2.94 (m, 4H), 2.69-2.55 (m, 2H), 2.36-2.24 (m, 2H).

Example 11

2-(3,5-Dichloropyridine-4-yl)-1-(7-methoxy-2',3',5',6'-tetrahydro-spiro[1,3-benzodioxole-2,4'-(4H)-thiopyran-1,1'-dioxide]-4-yl)ethanone (compound 112)

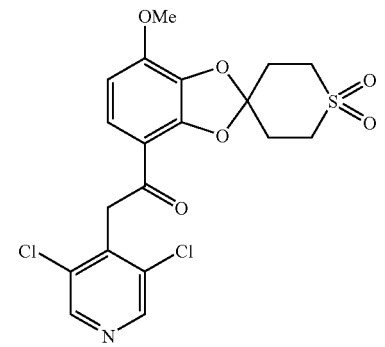

To a solution of 2-(3,5-dichloropyridine-4-yl)-1-(7-methoxy-2',3',5',6'-tetrahydro-spiro[1,3-benzodioxole-2,4'-(4H)-thiopyran]-4-yl)ethanone (11 mg, 26 μmol) in dichloromethane (0.25 mL) was added meta-chloroperbenzoic acid (10 mg, 58 μmol) and the reaction was stirred at room temperature overnight. Saturated aqueous NaHCO₃ (1 mL) was added, and the aqueous phase was extracted with dichloromethane (2×2 mL). The combined organic phase was dried over MgSO₄ and evaporated to dryness under reduced pressure. Standard HPLC purification afforded 2-(3,5-Dichloro-pyridine-4-yl)-1-(7-methoxy-2',3',5',6'-tetrahydro-spiro[1,3-benzodioxole-2,4'-(4H)-thiopyran-1',1'-dioxide]-4-yl) ethanone (5 mg, 42%). ¹H NMR (CDCl₃) δ 8.52 (s, 2H), 7.55 (d, 1H), 6.68 (d, 1H), 4.55 (s, 2H), 3.99 (s, 3H), 3.45-3.37 (m, 2H), 3.33-3.25 (m, 2H), 2.79-2.66 (m, 4H).

Example 12

2-(3,5-Dichloro-1-oxido-pyridine-4-yl)-1-(7-methoxy-2',3',5',6'-tetrahydro-spiro[1,3-benzodioxole-2,4'-(4H)-thiopyran-1',1'-dioxide]-4-yl)ethanone (compound 113)

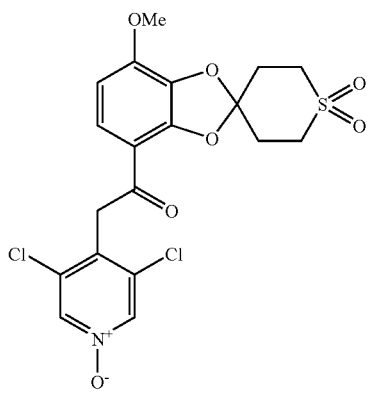

To a solution of 2-(3,5-dichloropyridine-4-yl)-1-(7-methoxy-2',3',5',6'-tetrahydro-spiro[1,3-benzodioxole-2,4'-(4H)-thiopyran]-4-yl)ethanone (10 mg, 23 μmol) in absolute ethanol (2 mL) was added first H₂O₂ (100 μL, 0.97 mmol) and then secondly methyltrioxorhenium(VII) (2 mg, 8 μmol). The mixture was stirred at 40° C. overnight before 5% W/V aqueous NaHSO₃ (10 mL) was added.

The aqueous phase was extracted with dichloromethane (3×20 mL). The combined organic phase was dried over MgSO₄ and evaporated to dryness under reduced pressure. Standard HPLC purification afforded 2-(3,5-dichloro-1-oxido-pyridine-4-yl)-1-(7-methoxy-2',3',5',6'-tetrahydro-spiro[1,3-benzodioxole-2,4'-(4H)-thiopyran-1',1'-dioxide]-4-yl)ethanone (2.5 mg, 23%). ¹H NMR (DMSO) δ 8.64 (s, 2H), 7.42 (d, 1H), 6.85 (d, 1H), 4.59 (s, 2H), 3.92 (s, 3H), 3.51 (m, 2H), 3.31 (m, 2H), 2.59 (m, 4H).

General Procedure A:

LiHMDS (1M in THF, 3.0 eq) was added dropwise to a ice-cold solution of the ester 512 (1 eq) and A-Methyl (1.3 eq) in anhydrous THF. The reaction mixture was stirred at rt for 12 h, H₂O (10 mL) and sat. aq. NH₄Cl (20 mL) were and then extracted with EtOAc (3×50 mL). The combined organic phases were dried (Na₂SO₄), filtered and concentrated under reduced pressure. The residue obtained was purified by flash column chromatography to afford ketone.

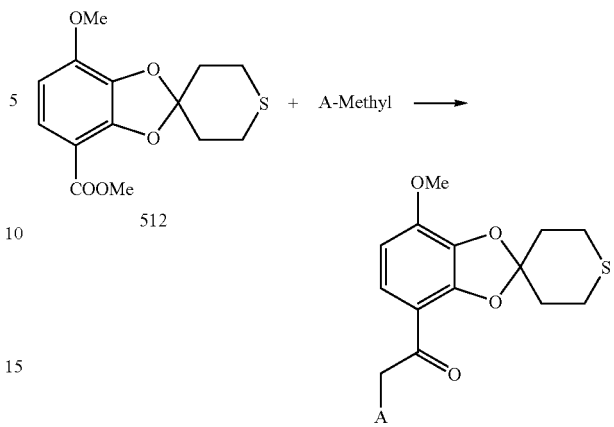

Example 13

2-(3-bromopyridine-4-yl)-1-(7-methoxy-2',3',5',6'-tetrahydro-spiro[1,3-benzodioxole-2,4'-(4H)-thiopyran]-4-yl)ethanone (compound 114)

Prepared according to General Procedure A using 18 mg of 4-bromo-3-methylpyridine (yield: 40%)

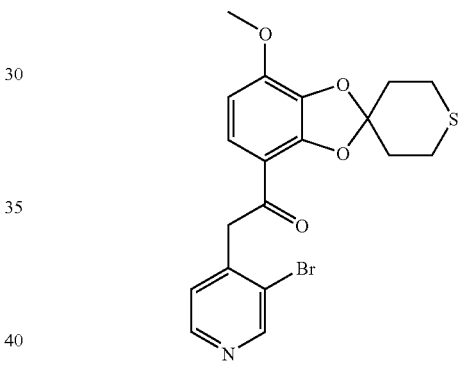

LC/MS (METHOD B): (m/z) 436.2 (MH+); RT=4.17 min; purity (UV)=100%

Example 14

2-(3-Bromo-pyrazin-2-yl))-1-(7-methoxy-2',3',5',6'-tetrahydro-spiro[1,3-benzodioxole-2,4'-(4H)-thiopyran]-4-yl)ethanone (compound 115)

Prepared according to General Procedure A using 17 mg of 2-bromo-3-methylpyrazine (yield: 9%)

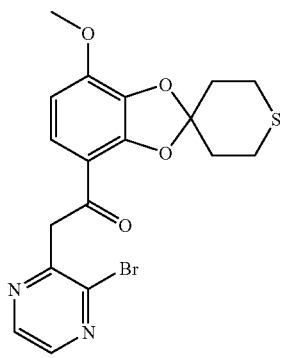

Example 15

2-(-pyrazin-2-yl)-1-(7-methoxy-2',3',5',6'-tetrahydro-spiro[1,3-benzodioxole-2,4'-(4H)-thiopyran]-4-yl)ethanone (compound 116)

Prepared according to General Procedure A using 16 mg of 2-methylpyrazine (yield: 52%)

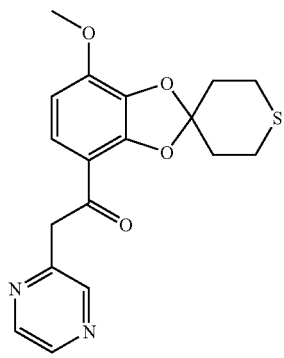

LC/MS (METHOD B): (m/z) 359.3 (MH+); RT=3.33 min; purity (UV)=100%

Example 16

2-(-pyridin-4-yl-)-1-(7-methoxy-2',3',5',6'-tetrahydro-spiro[1,3-benzo-dioxole-2,4'-(4H)-thiopyran]-4-yl)ethanone (compound 117)

Prepared according to General Procedure A using 18 mg of 4-methyl-pyridine (yield: 13%)

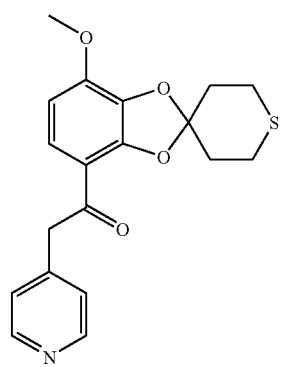

LC/MS (METHOD B): (m/z) 358.3 (MH+); RT=2.50 min; purity (UV)=100%

Example 17

2-(quinolin-4-yl-)-1-(7-methoxy-2',3',5',6'-tetrahydro-spiro[1,3-benzo-dioxole-2,4'-(4H)-thiopyran]-4-yl)ethanone (compound 118)

Prepared according to General Procedure A using 16 mg of 4-methylquinoline (yield: 12%)

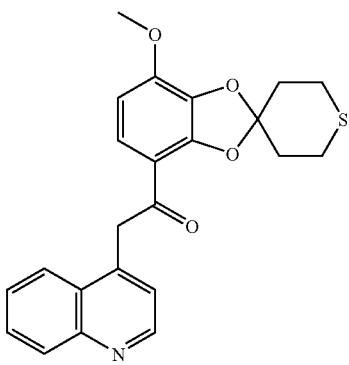

LC/MS (METHOD B): (m/z) 408.3 (MH+); RT=3.33 min; purity (UV)=100%

Example 18

2-(2,6-Dichloro-phenyl)-1-(7-methoxy-2',3',5',6'-tetrahydro-spiro[1,3-benzo-dioxole-2,4'-(4H)-thiopyran]-4-yl)ethanone (compound 119)

Prepared according to General Procedure A using 15 mg of 2,6-dichlorotoluene (yield: 8%)

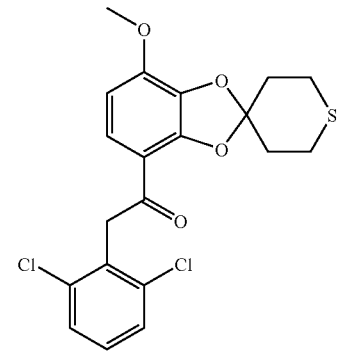

LC/MS (METHOD B): (m/z) 425.24 (MH+); RT=5.28 min; purity (UV)=100%

Example 19

2-(2-chloro-phenyl)-1-(7-methoxy-2',3',5',6'-tetrahydro-spiro[1,3-benzo-dioxole-2,4'-(4H)-thiopyran]-4-yl)ethanone (compound 120)

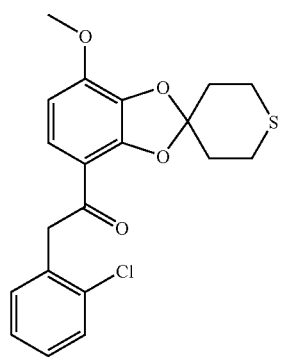

A solution of Methyl 7-methoxy-2',3',5',6'-tetrahydro-spiro[1,3-benzodioxole-2,4'-(4H)-thiopyran]-4-carboxylate (14 mg) in dry THF (500 mL) was cooled to 0° C. under Ar.

2-chlorobenzyl magnesiumchloride in diethyl ether (0.25M solution, 189 μL) was added and the cooling was removed. After 2 h at r.t. an additional portion of 2-chlorobenzyl magnesiumchloride in diethyl ether (0.25M solution, 189 μL) was added. The mixture was stirred for 18 h, added water and extracted with ethyl acetate. The combined organic phase was dried over MgSO$_4$ and evaporated to dryness under reduced pressure. Standard HPLC purification afforded compound 120 (9.2%).

LC/MS (METHOD B): (m/z) 391.22 (MH+); RT=4.90 min; purity (UV)=100%

Preparation 13

Methyl 2,3-dihydroxy-4-methoxybenzoate (compound 513)

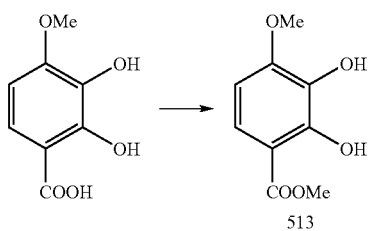

A solution of commercially available 2,3-dihydroxy-4-methoxybenzoic acid (11.6 g, 63 mmol) in anhydrous MeOH (150 mL) was cooled in an ice-bath and conc. H$_2$SO$_4$ (8 mL) added dropwise. The reaction mixture was refluxed for 12 h, then cooled to rt and the solvent was removed under reduced pressure. H$_2$O (100 mL) and sat aq NaHCO$_3$ (50 mL) were added and extracted with EtOAc (3×100 mL). The combined organic phase was dried (Na$_2$SO$_4$), filtered and concentrated in vacuo to afford compound 513 as a pale yellow solid, which was used in the next step without further purification. LC-MS: R$_T$=2.31 min.; m/z 197.3 (M−H)$^-$. $^1$H NMR (CDCl$_3$): δ 10.83 (1H, s), 7.41 (1H, d, J 9.0), 6.50 (1H, d, J 8.9), 5.45 (1H, s), 3.94 (3H, s), 3.93 (3H, s).

General Procedure B:

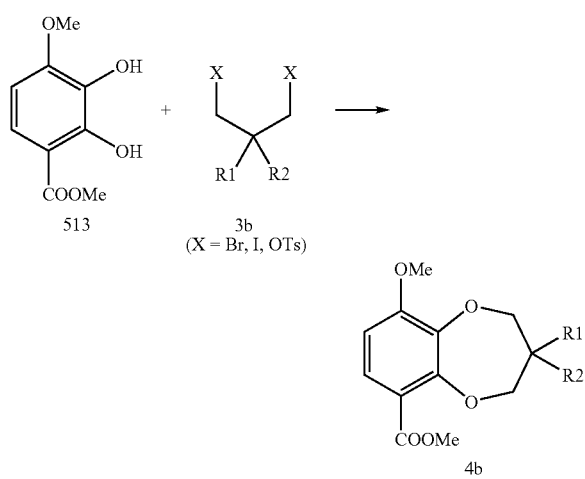

To a stirred solution of compound 513 and 3b (1.1 eq) in anhydrous DMSO was added K$_2$CO$_3$ (2.5 eq) and the mixture stirred at 100° C. for 4-12 h, under inert atmosphere. After cooling to rt, ice-water mixture was added, stirred for 15 min. and then extracted with EtOAc (3×50 mL). The combined organic phases were dried (Na$_2$SO$_4$), filtered and concentrated under reduced pressure. The residue obtained was purified by flash column chromatography.

Using general procedure B the following compounds were obtained:

Preparation 14

9-Methoxy-spiro[2H-1,5-benzodioxepin-3(4H),3'-oxetane]-6-carboxylic acid methyl ester (compound 514)

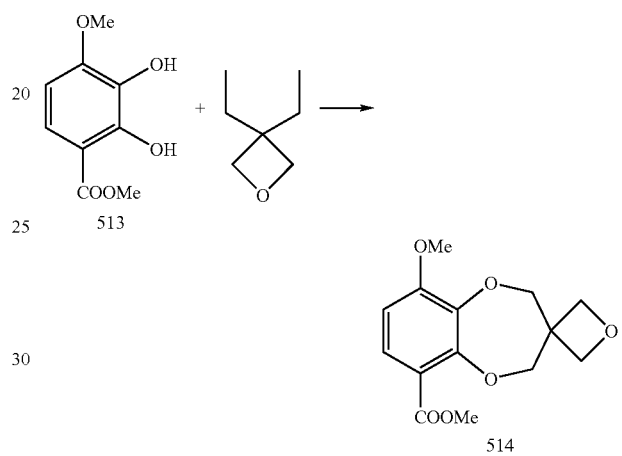

Following the general procedure, dialkylation of 513 (198 mg, 1 mmol) with commercial 3,3-bis(iodomethyl)oxetane (372 mg, 1.1 mmol) in DMSO (5 mL) in the presence of K$_2$CO$_3$ (345 mg, 2.5 mmol) afforded compound 514 as a white solid material after purification by column chromatography (50-65% EtOAc in light petroleum). LC-MS: R$_T$=2.40 min.; m/z 281.26 (M+H)$^+$. $^1$H NMR (CDCl$_3$): δ 7.49 (1H, d, J 8.8), 6.62 (1H, d, J 8.8), 4.61 (2H, d, J 6.8), 4.58 (2H, d, J 6.8), 4.48 (4H, s), 3.90 (3H, s), 3.87 (3H, s).

Preparation 15

9-Methoxy-spiro[2H-1,5-benzodioxepin-3(4H),3'-thietane]-6-carboxylic acid methyl ester (compound 516)

Step A:

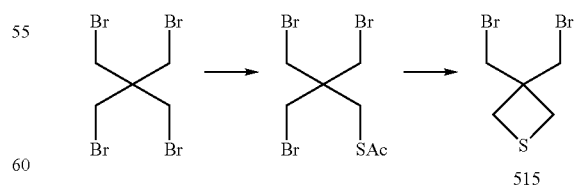

3,3-Bis(bromomethyl)thietane 515 was obtained in a two step process from 1,3-dibromo-2,2-bis(bromomethyl)propane following the literature procedure (Petrukhina, M. A.; Henck, C.; Li, B.; Block, E.; Jin, 3.; Zhang, S-Z.; Clerac, R. *Inorg. Chem.* 2005, 44, 77-84). Accordingly, a mixture of 1,3-dibromo-2,2-bis(bromomethyl)propane (7.76 g, 20 mmol) and KSAc (2.28 g, 20 mmol) in anhydrous THF (30 mL) was refluxed for 30 h. The ppt was filtered off and the filterate concentrated and the residue obtained was purified by flash column chromatography (10-25% EtOAc in light petroleum) to afford thioacetic acid(2,2-(bisbromomethyl)-3-bromopropyl)ester as a pale yellow solid material. A mixture of thioacetic acid(2,2-(bisbromomethyl)-3-bromopropyl)ester (1.53 g, 4 mmol) and NaOMe (324 mg, 6 mmol) in anhydrous MeOH (10 mL) was stirred at 0° C. for 2 h. MeOH was removed in vacuo, coevaporated with toluene (2×2 mL) and the residue obtained was filtered through a short pad of silica gel to give 3,3-bis(bromomethyl)thietane 515 as a thick oil, which was used without further purification.

Step B:

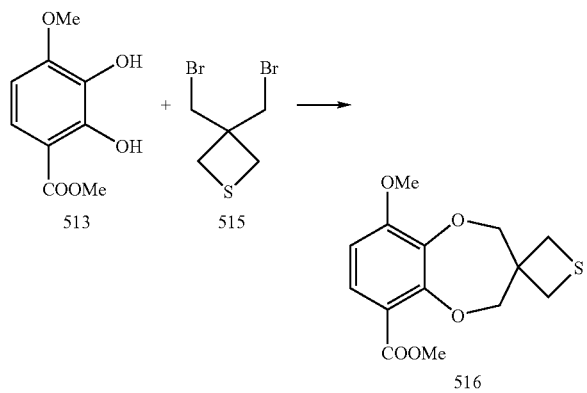

Following the general procedure, dialkylation of 513 (665 mg, 3.36 mmol) with 515 (962 mg, 3.7 mmol) in DMSO (15 mL) in the presence of $K_2CO_3$ (1.16 g, 8.4 mmol) afforded 516 as a white solid material after purification by column chromatography (40-60% EtOAc in light petroleum). LC-MS: $R_T$=3.17 min.; m/z 297.19 (M+H)$^+$. $^1$H NMR (CDCl$_3$): δ 7.49 (1H, d, J 8.8), 6.63 (1H, d, J 8.8), 4.30 (2H, s), 4.28 (2H, s), 3.90 (3H, s), 3.87 (3H, s), 3.11 (4H, s).

Preparation 16

9-Methoxy-spiro[2H-1,5-benzodioxepin-3(4H), 2'-(1,3-dioxolane)]-6-carboxylic acid methyl ester (compound 518)

Step A:

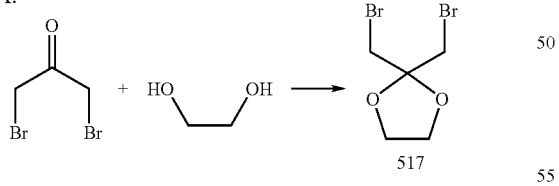

2,2-Bis(bromomethyl)-1,3-dioxolane 517 was obtained from dibromoacetone following the literature procedure (Valentin, M-L.; Bolte, J. Bull. Soc. Chim. Fr. 1995, 132, 1167-71). Accordingly, a solution of dibromoacetone (4.04 g, 18.7 mmol), ethylene glycol (2.32 g, 37.4 mmol) and p-TsOH (25 mg) in benzene (70 mL) was refluxed for 12 h, with azeotropic removal of water. The reaction mixture was concentrated under reduced pressure, Et$_2$O (50 mL) was added and the organic layer was washed with H$_2$O (2×50 mL), dried (Na$_2$SO$_4$), filtered and concentrated under reduced pressure. The residue obtained was purified by flash column chromatography (7-10% EtOAc in light petroleum) to afford 2,2-bis(bromomethyl)-1,3-dioxolane (517) as colourless liquid.

Step B:

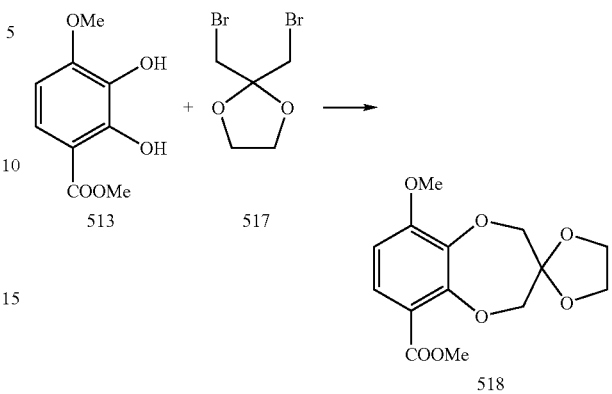

Following the general procedure, dialkylation of 513 (396 mg, 2 mmol) with 517 (572 mg, 2.2 mmol) in DMSO (10 mL) in the presence of $K_2CO_3$ (690 mg, 5 mmol) afforded 518 as a white solid material after purification by column chromatography (45-60% EtOAc in light petroleum). LC-MS: $R_T$=2.70 min.; m/z 297.18 (M+H)$^+$, 319.16 (M+Na)$^+$. $^1$H NMR (DMSO-d$_6$): δ 7.34 (1H, d, J 8.8), 6.76 (1H, d, J 8.8), 4.11 (2H, s), 4.09 (2H, s), 3.94 (4H, s), 3.80 (3H, s), 3.75 (3H, s).

Preparation 17

9-Methoxy-spiro[2H-1,5-benzodioxepin-3(4H),4'-tetrahydropyran]-6-carboxylic acid methyl ester (compound 520)

Step A:

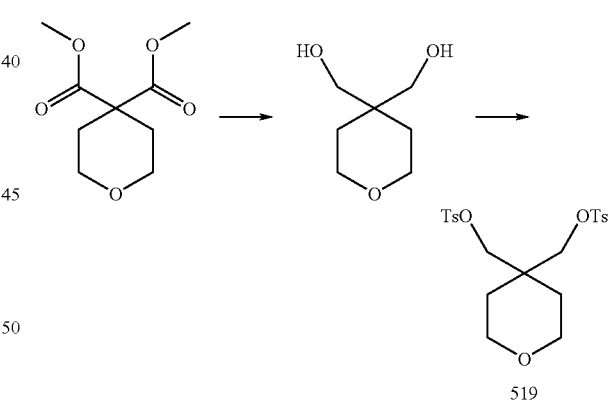

4,4-Bis(p-toluenesulphonyloxymethyl)tetrahydropyran (519) was obtained in a two step process from commercial tetrahydropyran-4,4-dicarboxalic acid dimethyl ester. Accordingly, to an ice-cooled solution of the diester (3.03 g, 15 mmol) in anhydrous toluene (45 mL) was added dropwise synhydride (70% in toluene, 19.5 mL, 66 mmol) and the mixture stirred at 120° C. for 3 h. The mixture was cooled to rt, H$_2$O (50 mL) was added slowly and concentrated over silica gel (35 g). Quick column chromatography with a linear gradient of MeOH in CH$_2$Cl$_2$ afforded 4,4-(bishydroxymethyl)tetrahydropyran as white solid material. A mixture of diol (1.46 g, 10 mmol) and TsCl (4.77 g, 25 mmol) in anhydrous pyridine (25 mL) was stirred at rt for 48 h. Solvent was removed in vacuo and co-evaporated with toluene (3×10 mL). CH$_2$Cl$_2$ (100 mL) and sat aq NaHCO$_3$ (100 mL) were added, the phases were separated and the organic phase was dried (Na$_2$SO$_4$), filtered and concentrated under reduced pressure. The residue obtained was flash chromatographed (35-45% EtOAc in light petroleum) to give 4,4-bis(p-toluenesulphonyloxymethyl)tetrahydropyran (519) as a white solid material.

Step B:

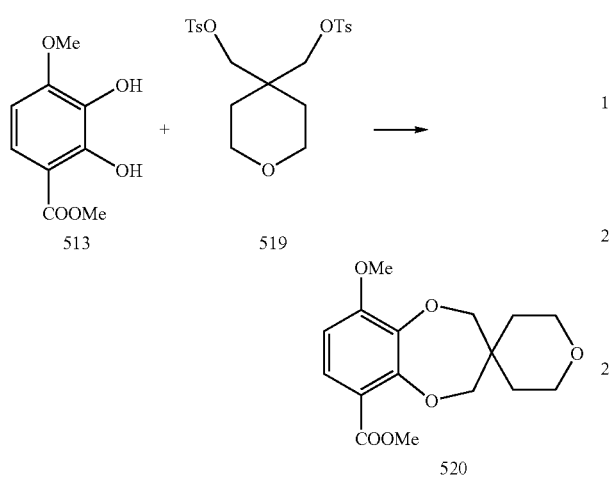

Following the general procedure, dialkylation of compound 513 (95 mg, 0.48 mmol) with compound 519 (240 mg, 0.53 mmol) in DMSO (3 mL) in the presence of K$_2$CO$_3$ (166 mg, 1.2 mmol) afforded compound 520 as a white solid material after purification by column chromatography (45-65% EtOAc in light petroleum). LC-MS: RT=2.40 min.; $^1$H NMR (DMSO-d$_6$): δ 7.34 (1H, d, J 8.8), 6.78 (1H, d, J 8.8), 3.99 (4H, s), 3.80 (3H, s), 3.76 (3H, s), 3.61 (4H, t, J 5.5), 1.54 (4H, t, J 5.5).

Preparation 18

9-Methoxy-2',2'-dimethyl-spiro[2H-1,5-benzodioxepin-3(4H),5'-[1,3]dioxane]-6-carboxylic acid methyl ester (compound 522)

Step A:

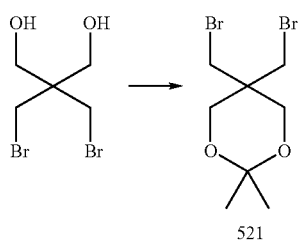

A solution of 2,2-bis(bromomethyl)-1,3-propanediol (5.0 g, 19.1 mmol), anhydrous acetone (20 mL) and p-TsOH (100 mg) in benzene (75 mL) was refluxed for 12 h, with azeotropic removal of water. The reaction mixture was concentrated under reduced pressure, EtOAc (100 mL) was added and the organic layer was washed successively with H$_2$O (3×30 mL) and brine (30 mL), dried (Na$_2$SO$_4$), filtered and concentrated under reduced pressure. The white solid obtained was triturated with n-pentane (20 mL) to afford 5,5-bis(bromomethyl)-2,2-dimethyl-[1,3]dioxane (521) as colourless crystals.

Step B:

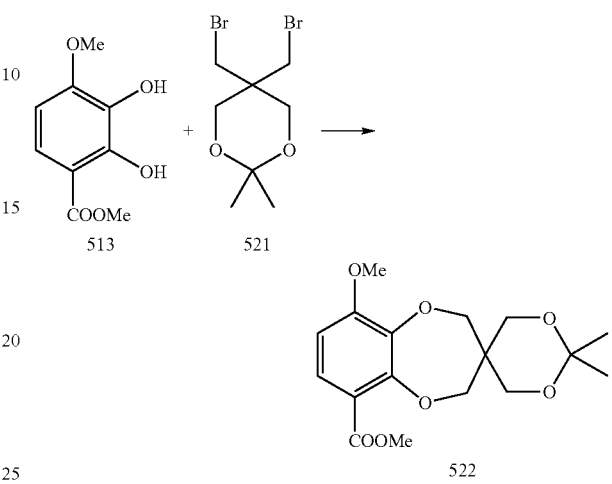

Following the general procedure, dialkylation of compound 513 (1.19 g, 6 mmol) with compound 521 (2.0 g, 6.62 mmol) in DMSO (30 mL) in the presence of K$_2$CO$_3$ (2.07 g, 15 mmol) afforded compound 522 as a white solid material after purification by column chromatography (30-40% EtOAc in light petroleum). LC-MS: R$_T$=2.99 min.; m/z 339.31 (M+H)$^+$, 361.25 (M+Na)$^+$. $^1$H NMR (CDCl$_3$): δ 7.45 (1H, d, J 8.8), 6.59 (1H, d, J 8.8), 4.22 (2H, s), 4.18 (2H, s), 3.89 (3H, s), 3.86 (7H, s), 1.43 (6H, s).

Preparation 19

9-Methoxy-spiro[2H-1,5-benzodioxepin-3(4H),5'-[1,3]dioxane]-6-carboxylic acid methyl ester (compound 524)

Step A:

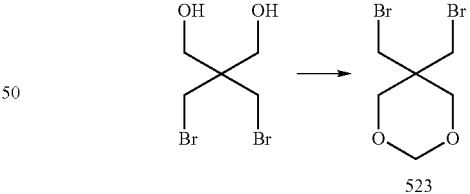

5,5-Bis(bromomethyl)-[1,3]dioxane (523) was obtained from 2,2-bis(bromomethyl)-1,3-propanediol following the literature procedure (Bitha, P.; Carvajal, S. G.; Citarella, R. V.; Delos Santos, E. F.; Durr, F. E.; Hlavka, J. J.; Lang, S. A., Jr.; Lindsay, H. L.; Thomas, J. P.; Wallace, R. E.; Yang-I, L. *J. Med. Chem.* 1989, 32(9), 2063-7 and Mitkin, O. D.; Wan, Y.; Kurchan, A. N.; Kutateladze, A. G. *Synthesis,* 2001, (8), 1133-42). Accordingly, a solution of 2,2-bis(bromomethyl)-1,3-propanediol (2.5 g, 9.55 mmol), formaldehyde (37% aqueous solution, 3.5 mL) and conc. HCl (2.0 mL) was refluxed for 12 h. After being cooled to rt, H$_2$O (25 mL) was added to the reaction mixture which was extracted with CH$_2$Cl$_2$ (2×25 mL). The combined organic layer successively washed with sat. aq. Na$_2$CO$_3$ (25 mL) and H$_2$O (25 mL), dried (Na$_2$SO$_4$), filtered and concentrated under reduced pressure. The colourless liquid obtained was found to be >95% pure by $^1$H NMR, and it was used without further purification.

Step B:

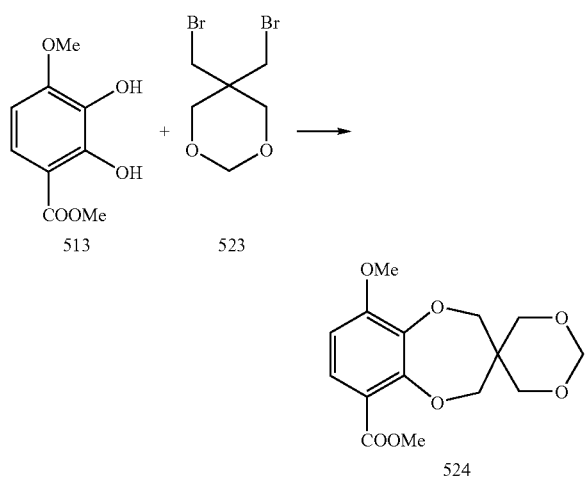

Following the general procedure, dialkylation of compound 513 (198 mg, 1 mmol) with compound 523 (301 mg, 1.1 mmol) in DMSO (5 mL) in the presence of K$_2$CO$_3$ (345 mg, 2.5 mmol) afforded compound 524 as a white solid material after purification by column chromatography (50-65% EtOAc in light petroleum). LC-MS: R$_T$=2.65 min.; m/z 311.23 (M+H)$^+$. $^1$H NMR (DMSO-d$_6$): 7.37 (1H, d, J 8.8), 6.81 (1H, d, J 8.8), 4.80 (1H, d, J 6.4), 4.78 (1H, d, J 6.4), 4.07 (2H, s), 4.01 (2H, s), 3.81 (7H, s), 3.76 (3H, s).

Preparation 20

9-Methoxy-spiro[2H-1,5-benzodioxepin-3(4H),5'-[1,3]dithiane]-6-carboxylic acid methyl ester (compound 526)

Step A:

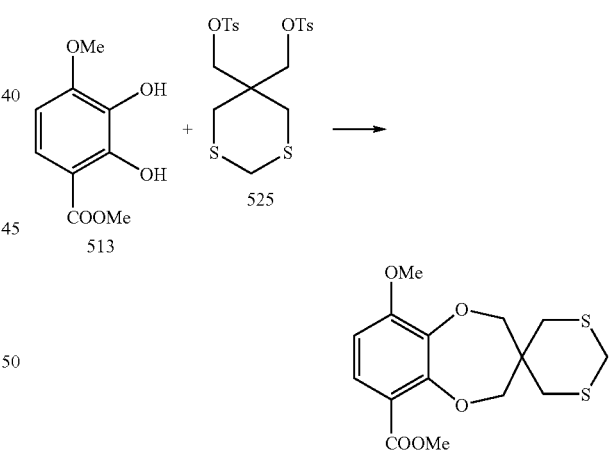

4,4-Bis(hydroxymethyl)-[1,3]dithiane was obtained in a two step process from compound 523 following the literature procedure (Mitkin, O. D.; Wan, Y.; Kurchan, A. N.; Kutateladze, A. G. *Synthesis*, 2001, (8), 1133-42). Accordingly, a mixture of compound 523 (1.36 g, 5 mmol) and KSAc (1.71 g, 15 mmol) in anhydrous DMF (10 mL) was stirred at rt for 30 h. The solvent was removed under reduced pressure and coevaporated with toluene (3×5 mL). Ice-water mixture was added and then extraction was performed with diisopropyl ether (2×25 mL). The combined organic phases were dried (Na$_2$SO$_4$), filtered and concentrated to afford 5,5-bis(acetylthiomethyl)-[1,3]dioxane (1.32 g, quantitative) as a pale yellow viscous oil. It was found to be >95% pure by $^1$H NMR and it was used without further purification.

A solution of 5,5-bis(acetylthiomethyl)-[1,3]dioxane (1.32 g, 5 mmol) in aq HCl (2N, 25 mL) was refluxed for 16 h and then cooled to rt. The mixture was made alkaline by dropwise addition of aq Na$_2$CO$_3$ (2M) and then extracted with CH$_2$Cl$_2$ (3×40 mL). The combined organic layer dried (Na$_2$SO$_4$), filtered and concentrated under reduced pressure to a white solid material, which was triturated with hot n-hexane-diisopropyl ether (2:1, 15 mL). The white solid was filtered to provide 4,4-bis(hydroxymethyl)-[1,3]dithiane, which was used without further purification.

A mixture of 4,4-bis(hydroxymethyl)-[1,3]dithiane (405 mg, 2.25 mmol) and TsCl (1.29 g, 6.75 mmol) in anhydrous pyridine (4 mL) was stirred at rt for 48 h. Solvent was removed in vacuo and co-evaporated with toluene (3×3 mL). CH$_2$Cl$_2$ (40 mL) and sat aq NaHCO$_3$ (40 mL) were added, the phases separated and the organic phase dried (Na$_2$SO$_4$), filtered and concentrated under reduced pressure. The residue obtained was flash chromatographed (35-55% EtOAc in light petroleum) to provide 4,4-bis(p-toluenesulphonyloxymethyl)-[1,3]dithiane (525) as a white solid material.

Step B:

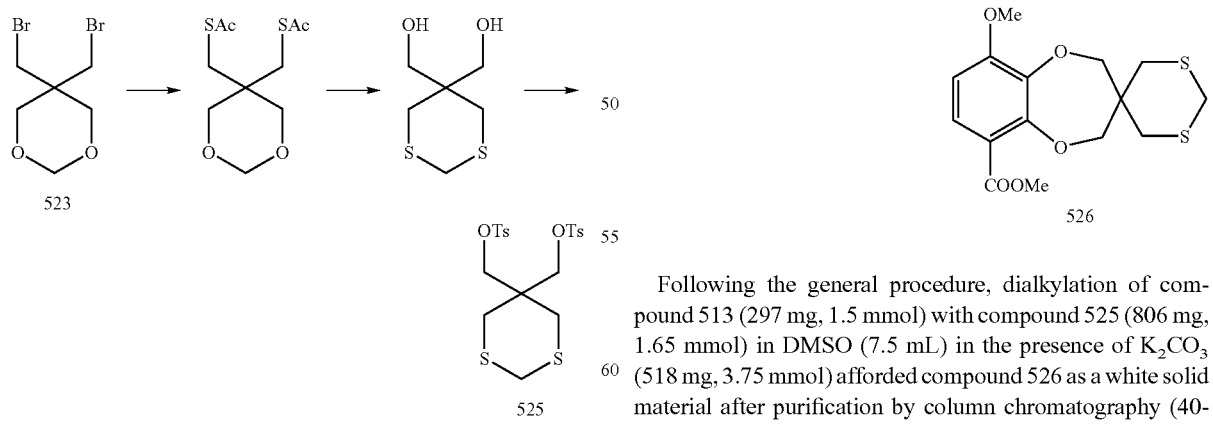

Following the general procedure, dialkylation of compound 513 (297 mg, 1.5 mmol) with compound 525 (806 mg, 1.65 mmol) in DMSO (7.5 mL) in the presence of K$_2$CO$_3$ (518 mg, 3.75 mmol) afforded compound 526 as a white solid material after purification by column chromatography (40-50% EtOAc in light petroleum). LC-MS: R$_T$=3.53 min.; m/z 343.14 (M+H)$^+$, 365.12 (M+Na)$^+$, 327.28 (M-CH$_3$)$^-$. $^1$H NMR (DMSO-d$_6$): δ 7.36 (1H, d, J 8.8), 6.81 (1H, d, J 8.8), 4.20 (2H, s), 4.14 (2H, s), 3.83 (2H, s), 3.81 (3H, s), 3.77 (3H, s), 2.85 (4H, s).

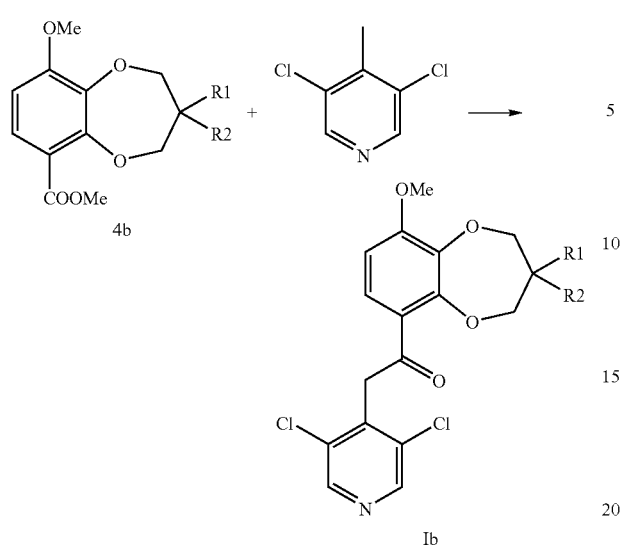

General Procedure C:

LiHMDS (1M in THF, 3.0 eq) was added dropwise to a ice-cold solution of ester 4b and commercially available 3,5-dichloro-4-methylpyridine (1.3 eq) in anhydrous THF. The reaction mixture was stirred at rt for 12 h, H$_2$O (10 mL) and sat. aq. NH$_4$Cl (20 mL) were added and the mixture was extracted with EtOAc (3×50 mL). The combined organic phases were dried (Na$_2$SO$_4$), filtered and concentrated under reduced pressure. The residue obtained was purified by flash column chromatography to afford ketone Ib.

Using general procedure C the following compounds were obtained:

Example 20

2-(3,5-Dichloropyridin-4-yl)-1-{9-methoxy-spiro[2H-1,5-benzodioxepin-3(4H),3'-oxetane]-6-yl}ethanone (compound 121)

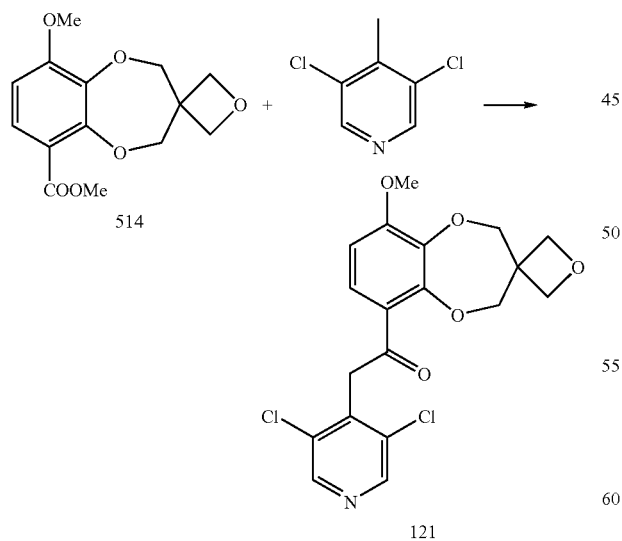

Following the general procedure, condensation of 3,5-dichloro-4-methylpyridine (169 mg, 1.04 mmol) with compound 514 (224 mg, 0.8 mmol) in THF (4 mL) in the presence of LiHMDS (2.4 mL, 2.4 mmol) afforded compound 121 as a white solid material after purification by column chromatography (65-80% EtOAc in light petroleum). LC-MS: R$_T$=3.24 min.; m/z 410.07 (M+H)$^+$, 408.19, 410.22 (M−H)$^-$. $^1$H NMR (DMSO-d$_6$): δ 8.66 (2H, s), 7.45 (1H, d, J 8.9), 6.91 (1H, d, J 9.0), 4.66 (2H, s), 4.57 (2H, s), 4.50 (2H, d, J 6.5), 4.46 (2H, d, J 6.5), 4.36 (2H, s), 3.85 (3H, s).

Example 21

2-(3,5-Dichloro-1-oxido-pyridin-4-yl)-1-{9-methoxy-spiro[2H-1,5-benzodioxepin-3(4H),3'-oxetane]-6-yl}ethanone (compound 122)

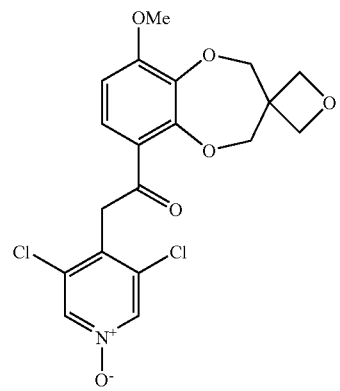

To a solution of 2-(3,5-Dichloropyridin-4-yl)-1-{9-methoxy-spiro[2H-1,5-benzodioxepin-3(4H),3'-oxetane]-6-yl}ethanone [121] (20.5 mg, 50 μmol) in CH$_2$Cl$_2$ (1 mL) was added 30% H$_2$O$_2$ (15 μL) and methyltrioxorhenium(VII) (5 mg). The mixture was stirred for 18 h, added MnO$_2$ (5 mg) and was stirred for another hour. CH$_2$Cl$_2$ (10 mL) was added and the organic phase was washed with water. The combined organic phase was dried over MgSO$_4$ and evaporated to dryness under reduced pressure. Standard HPLC purification afforded 14 mg of the product.

LC/MS (METHOD B): (m/z) 426.18; 428.20 (MH+); RT=2.42 min; purity (UV)=100%

Example 22

2-(3,5-Dichloropyridin-4-yl)-1-{9-methoxy-spiro[2H-1,5-benzodioxepin-3(4H),3'-thietane]-6-yl}ethanone (compound 123)

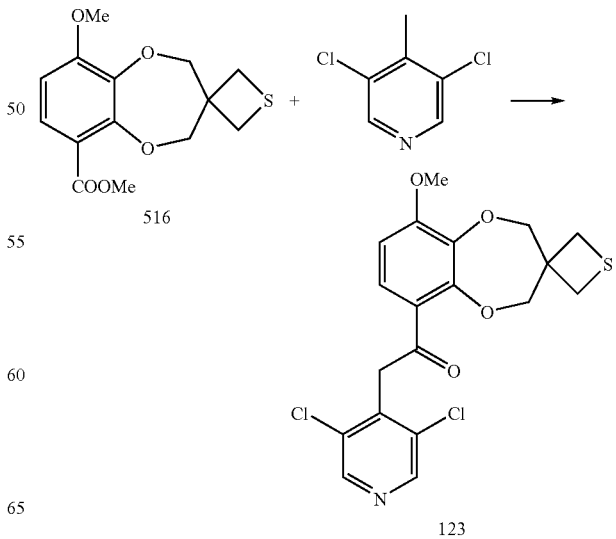

Following the general procedure, condensation of 3,5-dichloro-4-methylpyridine (366 mg, 2.26 mmol) with compound 516 (516 mg, 1.74 mmol) in THF (10 mL) in the presence of LiHMDS (5.2 mL, 5.2 mmol) afforded compound 123 as a white solid material after purification by column chromatography (55-65% EtOAc in light petroleum). LC-MS: $R_T$=4.23 min.; m/z 426.24, 428.25 (M+H)$^+$, 424.23 (M−H)$^−$. $^1$H NMR (CDCl$_3$): δ 8.51 (2H, s), 7.57 (1H, d, J 9.2), 6.71 (1H, d, J 9.2), 4.64 (2H, s), 4.46 (2H, s), 4.33 (2H, s), 3.93 (3H, s), 3.20 (2H, d, J 9.9), 3.12 (2H, d, J 9.9).

Example 23

2-(3,5-Dichloropyridin-4-yl)-1-{9-methoxy-spiro[2H-1,5-benzodioxepin-3(4H),3'-thietane-1',1'-dioxide]-6-yl}ethanone (compound 124)

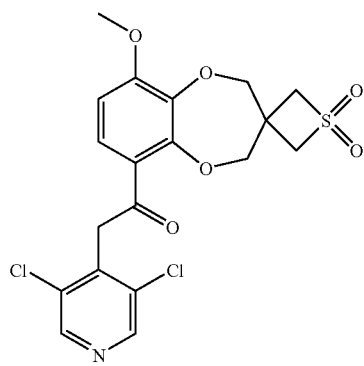

To a solution of 2-(3,5-Dichloropyridin-4-yl)-1-{9-methoxy-spiro[2H-1,5-benzodioxepin-3(4H),3'-thietane]-6-yl}ethanone [123] (42.6 mg) in CH$_2$Cl$_2$ (1 mL) was added 30% H$_2$O$_2$ (38 μL) and methyltrioxorhenium(VII) (5 mg). The mixture was stirred for 18 h and subsequently washed with water. The organic phase was dried over MgSO$_4$ and evaporated to dryness under reduced pressure. Standard HPLC purification afforded 6 mg of the product.

LC/MS (METHOD B): (m/z) 458.13, 460.10, 462.14 (MH+); RT=3.30 min; purity (UV)=100%

Example 24

2-(3,5-Dichloropyridin-1-oxido-4-yl)-1-{9-methoxy-spiro[2H-1,5-benzodioxepin-3(4H),3'-thietane-1',1'-dioxide]-6-yl}ethanone (compound 125)

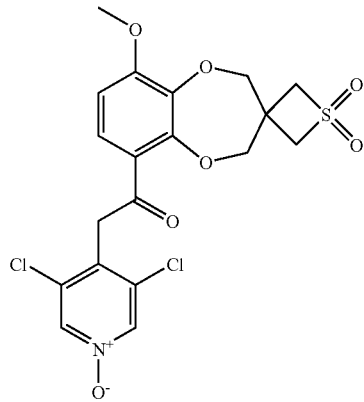

To a solution of 2-(3,5-Dichloropyridin-4-yl)-1-{9-methoxy-spiro[2H-1,5-benzodioxepin-3(4H),3'-thietane]-6-yl}ethanone [123] (39.6 mg) in CH$_2$Cl$_2$ (1 mL) was added 30% H$_2$O$_2$ (76 μL) and methyltrioxorhenium(VII) (5 mg). The mixture was stirred for 18 h, and was subsequently added water. The organic phase was dried over MgSO$_4$ and evaporated to dryness under reduced pressure. Standard HPLC purification afforded 8.4 mg of the product.

LC/MS (METHOD B): (m/z) 474.17, 476.16, 478.18 (MH+); RT=2.39 min; purity (UV)=100%

Example 25

2-(3,5-Dichloropyridin-4-yl)-1-{9-methoxy-spiro[2H-1,5-benzodioxepin-3(4H),2'-(1,3-dioxolane)]-6-yl}ethanone (compound 126)

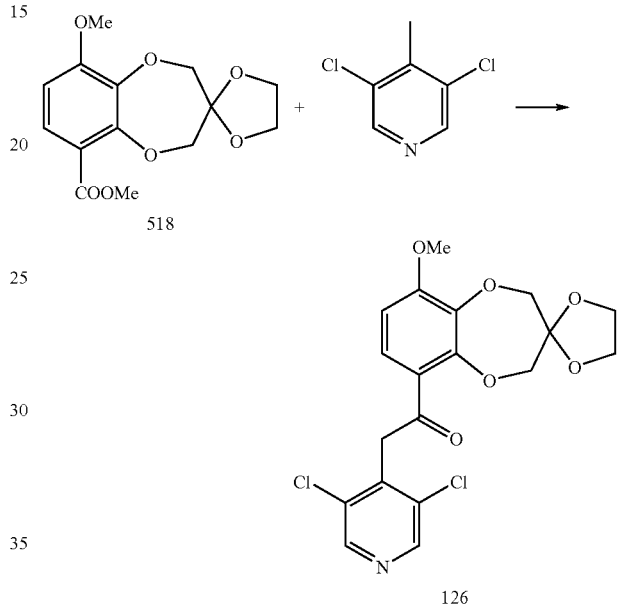

Following the general procedure, condensation of 3,5-dichloro-4-methylpyridine (53 mg, 0.33 mmol) with compound 518 (74 mg, 0.25 mmol) in THF (1.5 mL) in the presence of LiHMDS (0.75 mL, 0.75 mmol) afforded compound 126 as a white solid material after purification by column chromatography (60-80% EtOAc in light petroleum). LC-MS: $R_T$=3.63 min.; m/z 426.18, 428.16 (M+H)$^+$. $^1$H NMR (DMSO-d$_6$): δ 8.64 (2H, s), 7.39 (1H, d, J 8.8), 6.86 (1H, d, J 8.9), 4.60 (2H, s), 4.34 (2H, s), 4.17 (2H, s), 3.97 (4H, s), 3.84 (3H, s).

Example 26

2-(3,5-Dichloropyridin-4-yl)-1-{9-methoxy-spiro[2H-1,5-benzodioxepin-3(4H),4'-tetrahydropyran]-6-yl}ethanone (compound 127)

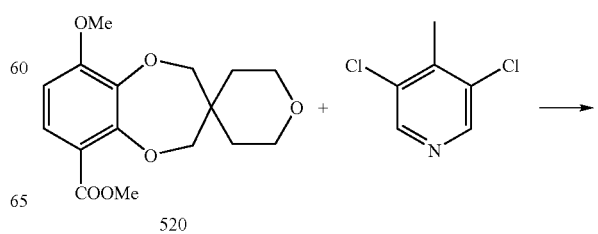

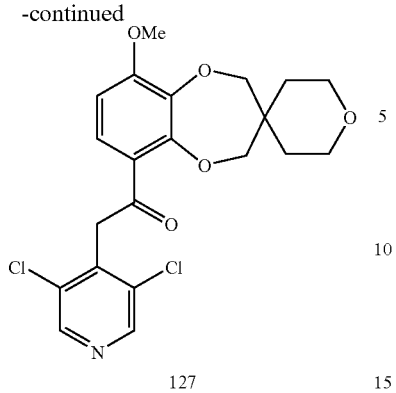

127

Following the general procedure, condensation of 3,5-dichloro-4-methylpyridine (59 mg, 0.36 mmol) with compound 520 (85 mg, 0.28 mmol) in THF (1.5 mL) in the presence of LiHMDS (0.85 mL, 0.85 mmol) afforded compound 127 as a white solid material after purification by column chromatography (60-70% EtOAc in light petroleum). LC-MS: $R_T$=3.70 min.; m/z 438.21, 440.21 (M+H)$^+$, 436.30, 438.27 (M−H)$^−$. $^1$H NMR (DMSO-d$_6$): δ 8.65 (2H, s), 7.42 (1H, d, J 8.9), 6.87 (1H, d, J 9.0), 4.63 (2H, s), 4.25 (2H, s), 4.07 (2H, s), 3.84 (3H, s), 3.64 (4H, t, J 5.3), 1.60 (4H, t, J 5.3).

Example 27

2-(3,5-Dichloro-1-oxido-pyridin-4-yl)-1-{9-methoxy-spiro[2H-1,5-benzodioxepin-3(4H),4'-tetrahydropyran]-6-yl}ethanone (compound 128)

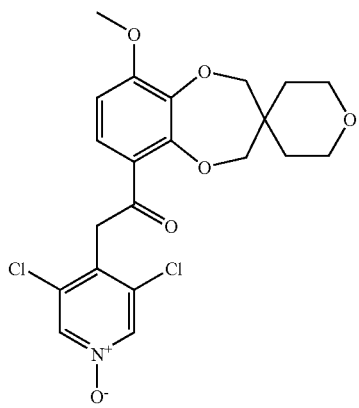

To a solution 2-(3,5-Dichloropyridin-4-yl)-1-{9-methoxy-spiro[2H-1,5-benzodioxepin-3(4H),4'-tetrahydropyran]-6-yl}ethanone [127] (66 mg, 150 μmmol) in CH$_2$Cl$_2$ (2 mL) was added 30% H$_2$O$_2$ (45 μL) and methyltrioxorhenium(VII) (10 mg). The mixture was stirred for 18 h, added MnO2 (10 mg) and was stirred for another hour. CH$_2$Cl$_2$ (10 mL) was added and the organic phase was washed with water. The combined organic phase was dried over MgSO$_4$ and evaporated to dryness under reduced pressure. Standard HPLC purification afforded 5.6 mg of the product.

LC/MS (METHOD B): (m/z) 454.32; 456.32 (MH+); RT=2.80 min; purity (UV)=100%

Example 28

2-(3,5-Dichloropyridin-4-yl)-1-{9-methoxy-2',2'-dimethyl-spiro[2H-1,5-benzodioxepin-3(4H),5'-[1,3]dioxane]-6-yl}ethanone (compound 129)

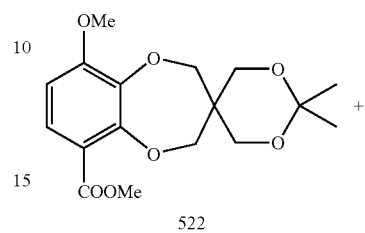

522

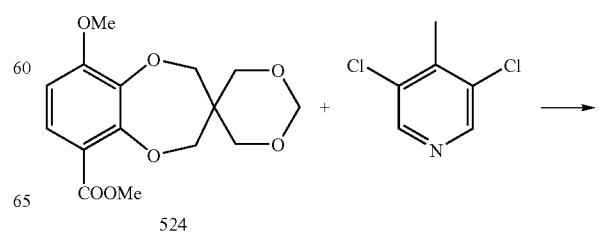

129

Following the general procedure, condensation of 3,5-dichloro-4-methylpyridine (93 mg, 0.58 mmol) with compound 522 (150 mg, 0.44 mmol) in THF (2 mL) in the presence of LiHMDS (1.3 mL, 1.3 mmol) afforded compound 129 as a white solid material after purification by column chromatography (55-60% EtOAc in light petroleum). LC-MS: $R_T$=3.95 min.; m/z 468.19, 470.23 (M+H)$^+$, 466.36, 468.33 (M−H)$^−$. $^1$H NMR (DMSO-d$_6$): δ 8.65 (2H, s), 7.42 (1H, d, J 8.8), 6.89 (1H, d, J 9.1), 4.63 (2H, s), 4.33 (2H, s), 4.08 (2H, s), 3.84 (3H, s), 3.82 (4H, s), 1.39 (3H, s), 1.37 (3H, s).

Example 29

2-(3,5-Dichloropyridin-4-yl)-1-{9-methoxy-spiro[2H-1,5-benzodioxepin-3(4H),5'-[1,3]dioxane]-6-yl}ethanone (compound 130)

524

-continued

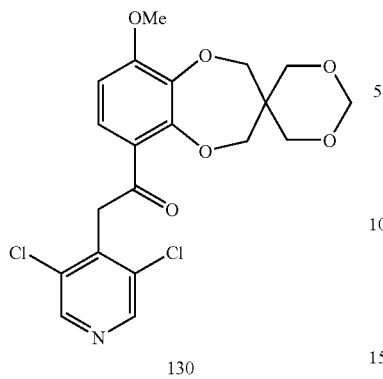

130

Following the general procedure, condensation of 3,5-dichloro-4-methylpyridine (211 mg, 1.3 mmol) with compound 524 (310 mg, 1.0 mmol) in THF (6 mL) in the presence of LiHMDS (3 mL, 3.0 mmol) afforded compound 130 as a white solid material after purification by column chromatography (60-80% EtOAc in light petroleum). LC-MS: $R_T$=3.64 min.; m/z 440.16, 442.17 (M+H)$^+$, 438.27, 440.29 (M−H). $^1$H NMR (DMSO-d$_6$): δ 8.65 (2H, s), 7.43 (1H, d, J 8.9), 6.89 (1H, d, J 8.9), 4.84 (1H, d, J 6.1), 4.79 (1H, d, J 6.1), 4.64 (2H, s), 4.34 (2H, s), 4.08 (2H, s), 3.90 (2H, d, J 11.4), 3.85 (3H, s), 3.82 (2H, d, J 11.2).

Example 30

2-(3,5-Dichloro-1-oxido-pyridine-4-yl)-1-{9-methoxy-spiro[2H-1,5-benzodioxepin-3(4H),5'-[1,3]dioxane]-6-yl}ethanone (compound 131)

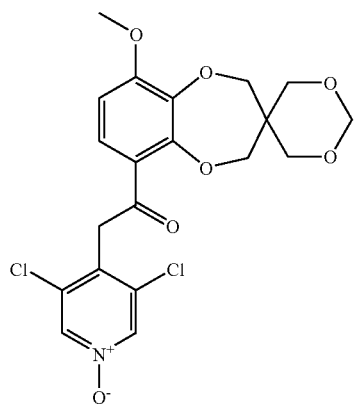

To a solution of 2-(3,5-Dichloropyridin-4-yl)-1-{9-methoxy-spiro[2H-1,5-benzodioxepin-3(4H),5'-[1,3]dioxane]-6-yl}ethanone [130] (100 mg) in CH$_2$Cl$_2$ (2 mL) was added 30% H$_2$O$_2$ (120 pt) and methyltrioxorhenium(VII) (5 mg). The mixture was stirred for 18 h and subsequently washed with water. The organic phase was dried over MgSO$_4$ and evaporated to dryness under reduced pressure. Standard HPLC purification afforded 85 mg of the product.

LC/MS (METHOD B): (m/z) 456.23 (MH+); RT=2.55 min; purity (UV)=95%

Example 31

2-(3,5-Dichloropyridin-4-yl)-1-{9-methoxy-spiro[2H-1,5-benzodioxepin-3(4H),5'-[1,3]dithiane]-6-yl}ethanone (compound 132)

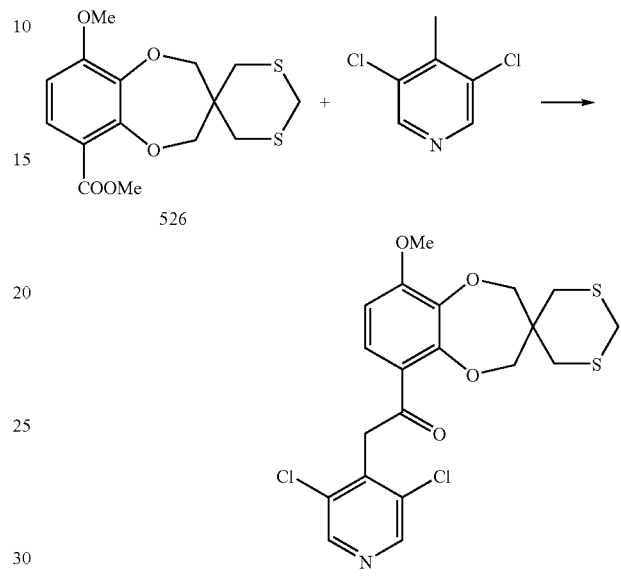

Following the general procedure, condensation of 3,5-dichloro-4-methylpyridine (154 mg, 0.95 mmol) with compound 526 (250 mg, 0.73 mmol) in THF (4 mL) in the presence of LiHMDS (2.2 mL, 2.2 mmol) afforded compound 132 as a white solid material after purification by column chromatography (45-55% EtOAc in light petroleum). LC-MS: $R_T$=4.39 min.; m/z 472.15, 474.14 (M+H)$^+$. $^1$H NMR (DMSO-d$_6$): δ 8.65 (2H, s), 7.42 (1H, d, J 8.9), 6.88 (1H, d, J 8.9), 4.64 (2H, s), 4.43 (2H, s), 4.24 (2H, s), 3.85 (3H, s), 3.84 (2H, s), 2.91 (4H, s).

Example 32

PDE4 Assay

Human recombinant PDE4 (Genbank accession no NM_006203) was incubated for 1 hour, with the test compound at concentrations up to 10 μM, with cAMP (1×10-5M), and with a low amount (0.021 MBq) of radioactively labelled cAMP. At the end of the incubation, the cleavage of the substrate was evaluated by the binding of the AMP product to SPA beads, which generate chemoluminescence when bound to the radioactive tracer. The AMP product inhibited the binding of the radioactive tracer to the beads, and the luminescent signal was competed. The results were calculated as the molar concentrations resulting in 50% inhibition of the substrate cleavage compared to controls samples, and are expressed as IC$_{50}$ (M).

The results are shown in Table 1 below.

TABLE 1

| Compound | IC$_{50}$ (PDE4) |
|---|---|
| 101 | 26 nM |
| 102 | 41 nM |
| 103 | 26 nM |
| 104 | 10 nM |
| 105 | 310 nM |
| 106 | 127 nM |
| 107 | 590 nM |
| 108 | 220 nM |
| 110 | 11 nM |
| 111 | 18 nM |
| 112 | 29 nM |
| 113 | 53 nM |
| 114 | 45 nM |
| 115 | 1410 nM |
| 116 | 1290 nM |
| 117 | 207 nM |
| 118 | 1800 nM |
| 119 | 71 nM |
| 120 | 310 nM |
| 121 | 52 nM |
| 122 | 50 nM |
| 123 | 17 nM |
| 124 | 104 nM |
| 125 | 200 nM |
| 126 | 67 nM |
| 127 | 22 nM |
| 128 | 11 nM |
| 129 |  |
| 130 | 40 nM |
| 131 | 43 nM |
| 132 | 26 nM |

Example 33

TNF-α Release

Human peripheral blood mononuclear cells (PBMC) were isolated from buffy coats. The blood is mixed with saline at a ratio of 1:1, and the PBMC were isolated using Lymphoprep Tubes™ (Nycomed, Norway). The PBMC were suspended in RPMI1640 with 2% foetal calf serum (FCS), pen/strep and 2 mM L-glutamine at a concentration of 5×105 c/ml. The cells were pre-incubated for 30 minutes with the test compounds in 96 well tissue culture plates and stimulated for 18 hours with lipopolysaccharide 1 mg/ml (Sigma). The level of TNF-α was measured in the culture supernatant by enzyme immunoassays using primary and secondary biotinylated antibodies from R&D systems. Results are expressed as IC$_{50}$ values calculated from inhibition curves using as positive controls the secretion in LPS stimulated wells and as negative controls the secretion in unstimulated cells.

The results are shown in Table 2 below.

TABLE 2

| Compound | IC$_{50}$ (TNF-α) |
|---|---|
| 101 | 28 nM |
| 102 | 88 nM |
| 103 | 23 nM |
| 104 | 44 nM |
| 105 | 800 nM |
| 106 | 158 nM |
| 107 | 910 nM |
| 108 | 167 nM |
| 110 | 17 nM |
| 111 | 19 nM |
| 112 | 34 nM |
| 113 | 82 nM |
| 114 | 95 nM |
| 115 | 471 nM |
| 116 | 2940 nM |
| 117 | 286 nM |
| 118 | 5520 nM |
| 119 | 508 nM |
| 120 | 1250 nM |
| 121 | 64 nM |
| 122 | 20 nM |
| 123 | 35 nM |
| 124 | 135 nM |
| 125 | 135 nM |
| 126 | 111 nM |
| 127 | 27 nM |
| 128 | 9 nM |
| 130 | 50 nM |
| 131 | 16 nM |
| 132 | 29 nM |

The invention claimed is:

1. A compound of formula (I)

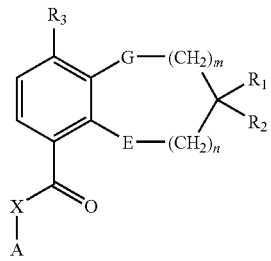

wherein m and n independently represent 0, 1, 2, 3, 4, 5, 6, or 7; and wherein G and E independently represent sulphur, oxygen, —N(R$_5$)—, or —N(R$_5$)C(O)—, and R$_1$ and R$_2$, together with the carbon atom to which they are attached, form a heterocyclic ring comprising one or two heteroatoms selected from oxygen, sulphur, —S(O)—, —S(O)$_2$—, —N=, —N(R$_5$)—, one or more carbon atoms in said heterocyclic ring being optionally substituted with one or more, same or different substituents selected from R$_4$;

R$_3$ is halogen, hydroxy, alkyl, alkenyl, alkynyl, haloalkyl, alkoxy, haloalkoxy, alkylthio, formyl, alkoxycarbonyl, alkylcarbonyl, or aminocarbonyl;

R$_4$ is hydrogen, amino, thioxo, alkyl, haloalkyl, hydroxyalkyl, alkoxy, halogen, oxo, thia, or hydroxy;

R$_5$ is hydrogen, alkyl, haloalkyl, alkylcarbonyl, hydroxyalkyl, alkoxycarbonyl, alkylsulfonyl, alkylaminosulfonyl or aminosulfonyl;

X is a bond, —CH$_2$—, or —NH—;

A is aryl, cycloalkyl, cycloalkenyl, arylalkyl, heteroaryl, heteroarylalkyl, heterocycloalkyl or heterocycloalkenyl, optionally substituted with one or more, same or different substituents selected from R$_4$; and pharmaceutically acceptable salts or N-oxides thereof.

2. A compound according to claim 1, wherein E and G are both oxygen.

3. A compound according to claim 1 or 2, wherein m and n are both one.

4. A compound according to claim 1 or 2, wherein m and n are both zero.

5. A compound according to claim 1, wherein $R_1$ and $R_2$, together with the carbon atom to which they are attached, form a heterocyclic ring comprising one or two heteroatoms selected from the group consisting of —O—, —S—, —S(O)—, —S(O$_2$)—, —N=, and —N(R$_5$)—; one or more carbon atoms in the heterocyclic ring being optionally substituted with one or more, same or different substituents selected from $R_4$.

6. A compound according to claim 1, wherein $R_1$ and $R_2$, together with the carbon atom to which they are attached, form a 4-, 5- or 6-membered heterocyclic ring.

7. A compound according to claim 5 or 6, wherein the heterocyclic ring is tetrahydropyran, oxetane, [1,3]dioxolane, [1,3]dioxane, tetrahydrothiopyran, tetrahydrothiopyran-1,1-dioxide, tetrahydrothiopyran-1-oxide, piperidine, tetrahydrothiophene, [1,3]-dithiane, thietane, [1,3]-dithiane-1,3-dioxide, thietane-1-oxide, or thiethane-1,1-dioxide.

8. A compound according to claim 5 or 6, wherein the heterocyclic ring comprises one heteroatom.

9. A compound according to claim 5 or 6, wherein the heterocyclic ring comprises two heteroatoms.

10. A compound according to claim 8, wherein the heteroatom(s) is/are oxygen.

11. A compound according to claim 8, wherein the heteroatom(s) is/are sulphur, —S(O)—, or —S(O)$_2$—.

12. A compound according to claim 1, wherein A is heteroaryl or heteroarylalkyl.

13. A compound according to claim 12, wherein A is pyridyl, pyrazinyl or quinolyl.

14. A compound according to claim 1, wherein A is phenyl.

15. A compound according to claim 1, wherein A is substituted with halogen.

16. A compound according to claim 1, wherein $R_3$ is $C_{1-6}$alkoxy, $C_{1-6}$halogenalkyl, or halogen.

17. A compound according to claim 16, wherein $R_3$ is methoxy or ethoxy.

18. A compound according to claim 1, wherein X is —CH$_2$—.

19. A compound according to claim 1, wherein X is —NH—.

20. A compound according to claim 13, wherein A is 4-(3,5-dichloropyridyl).

21. A compound according to claim 1, wherein $R_4$ is hydrogen.

22. A compound according to claim 1, selected from the group consisting of 2-(3,5-Dichloropyridine-4-yl)-1-(7-methoxy-2',3',5',6'-tetrahydro-spiro[1,3-benzodioxole-2,4'-(4H)-pyran]-4-yl)ethanone (compound 101), N-(3,5-Dichloropyridine-4-yl)-7-methoxy-2',3',5',6'-tetrahydro-spiro[1,3-benzodioxole-2,4'-(4H)-pyran]-4-carboxamide (compound 102), 2-(3,5-Dichloro-1-oxido-pyridine-4-yl)-1-(7-methoxy-2',3',5',6'-tetrahydro-spiro[1,3-benzo-dioxole-2,4'-(4H)-pyran]-4-yl)ethanone (compound 103), 2-(3,5-Dichloropyridine-4-yl)-1-(7-methoxy-4',5'-dihydro-spiro[1,3-benzodioxole-2,3'-(2H)-thiophen]-4-yl)ethanone (compound 104), 2-(3,5-Dichloropyridine-4-yl)-1-(7-methoxy-spiro[1,3-benzodioxole-2,4'-piperidine]-4-yl)ethanone (compound 105), 2-(3,5-Dichloropyridine-4-yl)-1-(7-methoxy-1'-[methoxycarbonyl]-spiro[1,3-benzodioxole-2,4'-piperidine]-4-yl)ethanone (compound 106), 2-(3,5-Dichloropyridine-4-yl)-1-(7-methoxy-1'-[methylsulfonyl]-spiro[1,3-benzodioxole-2,4'-piperidine]-4-yl)ethanone (compound 107), 2-(3,5-Dichloropyridine-4-yl)-1-(7-methoxy-1'-acetyl-spiro[1,3-benzodioxole-2,4'-piperidine]-4-yl)ethanone (compound 108)

2-(3,5-Dichloropyridin-4-yl)-1-(7-methoxy-1'-methyl-spiro[1,5-benzodioxole-2,4'-piperidine]-4-yl)ethanone (compound 109), 2-(3,5-Dichloropyridine-4-yl)-1-(7-methoxy-2',3',5',6'-tetrahydro-spiro[1,3-benzodioxole-2,4'-(4H)-thiopyran]-4-yl)ethanone (compound 110), 2-(3,5-Dichloropyridine-4-yl)-1-(7-methoxy-2',3',5',6'-tetrahydro-spiro[1,3-benzodioxole-2,4'-(4H)-thiopyran 1'-oxide]-4-yl)ethanone. (compound 111), 2-(3,5-Dichloropyridine-4-yl)-1-(7-methoxy-2',3',5',6'-tetrahydro-spiro[1,3-benzodioxole-2,4'-(4H)-thiopyran-1',1'-dioxide]-4-yl)ethanone (compound 112), 2-(3,5-Dichloro-1-oxido-pyridine-4-yl)-1-(7-methoxy-2',3',5',6'-tetrahydro-spiro[1,3-benzo-dioxole-2,4'-(4H)-thiopyran-1',1'-dioxide]-4-yl)ethanone (compound 113), 2-(3-bromopyridine-4-yl)-1-(7-methoxy-2',3',5',6'-tetrahydro-spiro[1,3-benzodioxole-2,4'-(4H)-thiopyran]-4-yl)ethanone (compound 114), 2-(3-Bromo-pyrazin-2-yl))-1-(7-methoxy-2',3',5',6'-tetrahydro-spiro[1,3-benzodioxole-2,4'-(4H)-thiopyran]-4-yl)ethanone (compound 115), 2-(-pyrazin-2-yl)-1-(7-methoxy-2',3',5',6'-tetrahydro-spiro[1,3-benzodioxole-2,4'-(4H)-thiopyran]-4-yl)ethanone (compound 116), 2-(-pyridin-4-yl-)-1-(7-methoxy-2',3',5',6'-tetrahydro-spiro[1,3-benzodioxole-2,4'-(4H)-thiopyran]-4-yl)ethanone (compound 117), 2-(quinolin-4-yl-)-1-(7-methoxy-2',3',5',6'-tetrahydro-spiro[1,3-benzodioxole-2,4-(4H)-thiopyran]-4-yl)ethanone (compound 118), 2-(2,6-Dichloro-phenyl)-1-(7-methoxy-2',3',5',6'-tetrahydro-spiro[1,3-benzodioxole-2, 4'-(4H)-thiopyran]-4-yl)ethanone (compound 119), 2-(2-Chloro-phenyl)-1-(7-methoxy-2',3',5',6'-tetrahydro-spiro[1,3-benzodioxole-2,4'-(4H)-thiopyran]-4-yl)ethanone (compound 120), 2-(3,5-Dichloropyridin-4-yl)-1-{9-methoxy-spiro[2H-1,5-benzodioxepin-3(4H),3'-oxetane]-6-yl}ethanone (compound 121), 2-(3,5-Dichloro-1-oxido-pyridin-4-yl)-1-{9-methoxy-spiro[2H-1,5-benzodioxepin-3 (4E),3'-oxetane]-6-yl}ethanone (compound 122), 2-(3,5-Dichloropyridin-4-yl)-1-{9-methoxy-spiro[2H-1,5-benzodioxepin-3(4H),3'-thietane]-6-yl}ethanone (compound 123), 2-(3,5-Dichloropyridin-4-yl)-1-{9-methoxy-spiro[2H-1,5-benzodioxepin-3(4H),3'-thietane-1', 1'-dioxide]-6-yl}ethanone (compound 124), 2-(3,5-Dichloropyridin-1-oxido-4-yl)-1-{9-methoxy-spiro[2H-1,5-benzodioxepin-3(4H),3'-thietane-1',1'-dioxide]-6-yl}ethanone (compound 125), 2-(3,5-Dichloropyridin-4-yl)-1-{9-methoxy-spiro[2H-1,5-benzodioxepin-3(4H),2'-(1,3-dioxolane)]-6-yl}ethanone (compound 126), 2-(3,5-Dichloropyridin-4-yl)-1-{9-methoxy-spiro[2H-1,5-benzodioxepin-3(4H),4'-tetrahydropyran]-6-yl}ethanone (compound 127), 2-(3,5-Dichloro-1-oxido-pyridin-4-yl)-1-{9-methoxy-spiro[2H-1,5-benzodioxepin-3(4H),4'-tetrahydropyran]-6-yl}ethanone (compound 128), 2-(3,5-Dichloropyridin-4-yl)-1-{9-methoxy-2',2'-dimethyl-spiro[2H-1,5-benzodioxepin-3(4H),5'-[1,3]dioxane]-6-yl}ethanone (compound 129), 2-(3,5-Dichloropyridin-4-yl)-1-{9-methoxy-spiro[2H-1,
   5-benzodioxepin-3(4H),5'-[1,3]dioxane]-6-
   yl}ethanone (compound 130),
2-(3,5-Dichloro-1-oxido-pyridine-4-yl)-1-{9-methoxy-
   spiro[2H-1,5-benzodioxepin-3(4H),5'-[1,3]dioxane]-6-
   yl}ethanone (compound 131), and
2-(3,5-Dichloropyridin-4-yl)-1-{9-methoxy-spiro[2H-1,
   5-benzodioxepin-3(4H),5'-[1,3]dithiane]-6-
   yl}ethanone (compound 132),
and pharmaceutically acceptable salts or N-oxides thereof.

23. A compound according to claim 1 with a molecular weight below 800 Dalton.

24. A compound according to claim 1 for use in therapy.

25. A pharmaceutical composition comprising a compound according to claim 1 together with a pharmaceutically acceptable excipient or vehicle or pharmaceutically acceptable carrier(s).

* * * * *